US011771886B2

(12) United States Patent
Volosin et al.

(10) Patent No.: US 11,771,886 B2
(45) Date of Patent: Oct. 3, 2023

(54) MEDICAL DEVICES WITH RAPID SENSOR RECOVERY

(71) Applicant: ZOLL MEDICAL CORPORATION, Chelmsford, MA (US)

(72) Inventors: Kent Volosin, Mars, PA (US); Shane S. Volpe, Saltsburg, PA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 264 days.

(21) Appl. No.: 16/832,476

(22) Filed: Mar. 27, 2020

(65) Prior Publication Data

US 2020/0222684 A1 Jul. 16, 2020

Related U.S. Application Data

(63) Continuation of application No. 15/827,519, filed on Nov. 30, 2017, now Pat. No. 10,646,707.

(51) Int. Cl.
*A61N 1/39* (2006.01)
*A61N 1/04* (2006.01)
(Continued)

(52) U.S. Cl.
CPC ............ *A61N 1/046* (2013.01); *A61B 5/0006* (2013.01); *A61N 1/3904* (2017.08); *A61B 5/024* (2013.01);
(Continued)

(58) Field of Classification Search
CPC .. A61N 1/3904; A61N 1/3625; A61N 1/3716; A61N 1/046; A61N 1/0476; A61N 1/0484; A61N 1/0492; A61N 1/0496
See application file for complete search history.

(56) References Cited

U.S. PATENT DOCUMENTS 3,241,556 A 3/1966 Zacouto
3,460,542 A 8/1969 Gemmer
(Continued)

FOREIGN PATENT DOCUMENTS

EP 396048 A1 11/1990
EP 0335356 A2 3/1996
(Continued)

OTHER PUBLICATIONS

International Preliminary Report on Patentability for Application No. PCT/US2018/062763 dated Jun. 2, 2020, 8 pages.
(Continued)

*Primary Examiner* — George R Evanisko
(74) *Attorney, Agent, or Firm* — FINCH & MALONEY PLLC

(57) ABSTRACT

Techniques that enable medical devices to quickly recover from loss of sensory functions are provided. In some examples, a medical device is configured to advantageously leverage differences between a first type of sensing electrode and a second type of sensing electrode that has a shorter recovery time than the first type of sensing electrode. In some examples, a medical device is configured to reference data generated by a first conditioning circuit that is configured to process signals acquired under a first set of environmental conditions and to reference data generated by a second conditioning circuit that is configured to process signal acquired under a second set of environmental conditions. In some examples, a medical device is configured to arrange electrodes used by the medical device to acquire signals in at specific locations to reduce the amount of disruptive power the electrodes encounter.

19 Claims, 13 Drawing Sheets

(51) Int. Cl.

| | |
|---|---|
| *A61B 5/00* | (2006.01) |
| *A61B 34/10* | (2016.01) |
| *A61B 5/024* | (2006.01) |
| *A61B 5/11* | (2006.01) |
| *A61N 1/38* | (2006.01) |
| *A61B 5/318* | (2021.01) |
| *A61B 5/361* | (2021.01) |
| *A61B 5/363* | (2021.01) |

(52) U.S. Cl.
CPC ............. *A61B 5/1118* (2013.01); *A61B 5/318* (2021.01); *A61B 5/361* (2021.01); *A61B 5/363* (2021.01); *A61B 5/4836* (2013.01); *A61B 5/6831* (2013.01); *A61B 34/10* (2016.02); *A61N 1/385* (2013.01)

(56) References Cited

U.S. PATENT DOCUMENTS

| | | |
|---|---|---|
| 3,702,613 A | 11/1972 | Panico et al. |
| 3,744,482 A | 7/1973 | Kaufman et al. |
| 3,826,245 A | 7/1974 | Funfstuck |
| 3,942,533 A | 3/1976 | Cannon, III |
| 3,961,623 A | 6/1976 | Milani et al. |
| 4,576,170 A | 3/1986 | Bradley et al. |
| 4,580,572 A | 4/1986 | Granek et al. |
| 4,583,547 A | 4/1986 | Granek et al. |
| 4,729,377 A | 3/1988 | Granek et al. |
| 4,928,690 A * | 5/1990 | Heilman ............... A61B 5/6831 607/4 |
| 4,991,217 A | 2/1991 | Garrett et al. |
| 5,078,134 A | 1/1992 | Heilman et al. |
| 5,558,098 A | 9/1996 | Fain |
| 5,741,306 A | 4/1998 | Glegyak et al. |
| 5,929,601 A | 7/1999 | Kaib et al. |
| 5,944,669 A | 8/1999 | Kaib |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen |
| 6,178,343 B1 | 1/2001 | Bindszus et al. |
| 6,253,099 B1 | 6/2001 | Oskin et al. |
| 6,280,461 B1 | 8/2001 | Glegyak et al. |
| 6,336,900 B1 | 1/2002 | Alleckson et al. |
| 6,374,138 B1 | 4/2002 | Owen |
| 6,406,426 B1 | 6/2002 | Reuss et al. |
| 6,546,285 B1 | 4/2003 | Owen |
| 6,681,003 B2 | 1/2004 | Linder et al. |
| 6,865,413 B2 | 3/2005 | Halperin et al. |
| 6,889,078 B2 | 5/2005 | Struble et al. |
| 6,889,079 B2 | 5/2005 | Bocek et al. |
| 6,908,437 B2 | 6/2005 | Bardy |
| 6,925,330 B2 | 8/2005 | Kleine |
| 7,149,579 B1 | 12/2006 | Koh et al. |
| 7,295,871 B2 | 11/2007 | Halperin et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,534,212 B2 | 5/2009 | Baker, Jr. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,406,842 B2 | 3/2013 | Kaib et al. |
| 8,600,486 B2 | 12/2013 | Kaib |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 9,161,723 B2 | 10/2015 | Rodriguez-Llorente et al. |
| 10,646,707 B2 * | 5/2020 | Volosin ................. A61N 1/3904 |
| 2001/0031991 A1 | 10/2001 | Russial |
| 2003/0004547 A1 | 1/2003 | Owen |
| 2003/0032988 A1 | 2/2003 | Fincke |
| 2003/0095648 A1 | 5/2003 | Kaib et al. |
| 2003/0149462 A1 | 8/2003 | White et al. |
| 2004/0010294 A1 | 1/2004 | Kleine |
| 2005/0049644 A1 | 3/2005 | Warren et al. |
| 2005/0131465 A1 | 6/2005 | Freeman et al. |
| 2005/0288599 A1 | 12/2005 | MacAdam et al. |
| 2006/0178706 A1 | 8/2006 | Lisogurski et al. |
| 2006/0211934 A1 | 9/2006 | Hassonjee et al. |
| 2007/0016029 A1 | 1/2007 | Donaldson et al. |
| 2007/0073120 A1 | 3/2007 | Li et al. |
| 2007/0239220 A1 | 10/2007 | Greenhut et al. |
| 2008/0004536 A1 | 1/2008 | Baxi et al. |
| 2008/0033495 A1 | 2/2008 | Kumar |
| 2008/0183090 A1 | 7/2008 | Farringdon et al. |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0076345 A1 | 3/2009 | Manicka et al. |
| 2009/0076363 A1 | 3/2009 | Bly et al. |
| 2009/0076559 A1 | 3/2009 | Libbus et al. |
| 2009/0234410 A1 | 9/2009 | Libbus et al. |
| 2009/0026479 A1 | 10/2009 | Mazar |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0052892 A1 | 3/2010 | Allen et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0114243 A1 | 5/2010 | Nowak et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0170692 A1 | 7/2011 | Konrad et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0085538 A1 | 4/2013 | Volpe et al. |
| 2013/0113496 A1 | 5/2013 | Craige, III et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0206974 A1 | 7/2014 | Volpe et al. |
| 2014/0249613 A1 | 9/2014 | Kaib |
| 2014/0277243 A1 | 9/2014 | Maskara et al. |
| 2014/0303680 A1 | 10/2014 | Donnelly et al. |
| 2014/0324112 A1 | 10/2014 | Macho et al. |
| 2015/0005588 A1 | 1/2015 | Herken et al. |
| 2015/0035654 A1 | 2/2015 | Kaib et al. |
| 2015/0039042 A1 | 2/2015 | Amsler et al. |
| 2015/0039053 A1 | 2/2015 | Kaib et al. |

(56) References Cited

U.S. PATENT DOCUMENTS

2015/0080699 A1 3/2015 Kaib et al.
2015/0224330 A1 8/2015 Kaib et al.

FOREIGN PATENT DOCUMENTS

| | | | |
|---|---|---|---|
| EP | 1720446 | B1 | 7/2010 |
| JP | 5115450 | A | 5/1993 |
| JP | 2002514107 | A | 5/2002 |
| JP | 2008302225 | A | 12/2008 |
| JP | 2008302228 | A | 12/2008 |
| JP | 2009510631 | A | 3/2009 |
| WO | 83/04171 | A1 | 12/1983 |
| WO | 1998039061 | A2 | 9/1998 |
| WO | 2004054656 | A1 | 7/2004 |
| WO | 2004078259 | A1 | 9/2004 |
| WO | 2006050325 | A2 | 5/2006 |
| WO | 2009122277 | A2 | 10/2009 |
| WO | 2012006524 | A1 | 1/2012 |
| WO | 2013130957 | A2 | 9/2013 |
| WO | 2014097035 | A1 | 6/2014 |

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

http://web.archive.org/web/20030427001846/http:/www.lifecor.comiimagelib/imageproduct.asp. Published by LifeCor, Inc., 2002, on a webpage owned by LifeCor, Inc.

Association for the Advancement of Medical Instrumentation, ANSI/AAMI DF80:2003 Medical Elecliical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

Zoll Medical Corporation, LifeVest Model WCD 3000 Operator's Manual, Pittsburgh, PA, 2012, 176 pages.

Deeksha Gupta et al., "Design of Sub-Circuits of Switched Capacitor Filter and its Application in ECG Using 0.18μm CMOS Technology", Int. Journal of Innovative Research in Science, Engineering and Technology, Jul. 2016, 5 pages, vol. 5, Issue 7.

Willem G. de Voogt et al., "Understanding Capture Detection", The European Society of Cardiology, 2004, 9 pages, Elsevier.

L.A. Geddes et al., "Principles of Applied Biomedical Instrumentation", 3rd Edition, 1968, Chapter 9, pp. 315-377.

Enrique Spinelli et al., "A Capacitive Electrode with Fast Recovery Feature", Institute of Physics and Engineering in Medicine, 2012, pp. 1277-1288.

David M. Beams, "Pacemaker Sense Amplifiers", University of Wisconsin, 2014, Chapters, 48 pages.

International Search Report and Written Opinion Received for PCT Application No. PCT/US18/62763, dated Feb. 11, 2019. 11 pages.

Extended European Search Report for Application No. 18882364.5 dated Jul. 20, 2021, 6 pages.

* cited by examiner

| Sensing Electrode Type | BPM | Pulse Duration (msec) | Pacing Energy (mA) | ECG Signal Recovery Time |
|---|---|---|---|---|
| Dry | 90 | 50 | 140 | ~500 msec |
| Dry | 90 | 40 | 80 | ~500 msec |
| Dry | 90 | 40 | 100 | ~500 msec |
| Dry | 90 | 50 | 120 | ~500 msec |
| Conductive | 85 | 50 | 140 | ~300 msec |
| Conductive | 85 | 50 | 140 | ~300 msec |
| Conductive | 85 | 50 | 140 | ~300 msec |

FIG. 7

MEDICAL DEVICES WITH RAPID SENSOR RECOVERY

RELATED APPLICATION

This application is a Continuation Application of U.S. Non-Provisional application Ser. No. 15/827,519, titled "MEDICAL DEVICES WITH RAPID SENSOR RECOVERY," filed Nov. 30, 2017, the content of which is incorporated herein by reference in its entirety.

BACKGROUND

The present disclosure is directed to sensing electrodes and the use thereof in medical devices.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

Ventricular fibrillation is one of the deadliest cardiac arrhythmias known. Ventricular fibrillation occurs when normal, regular electrical impulses are replaced by irregular and rapid impulses, which cause the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators, such as manual defibrillators or automated external defibrillators (AEDs) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

SUMMARY

In one example, an ambulatory medical device is provided. The ambulatory medical device includes at least one therapy electrode, at least two first sensing electrodes, at least two second sensing electrodes, and at least one processor. The at least one therapy electrode is configured to couple externally to a skin of a patient to provide one or more therapeutic stimulation pulses to a heart of the patient during execution of a treatment protocol. The at least two first sensing electrodes are distinct from the at least one therapy electrode and are configured to couple externally to the skin of the patient to acquire first electrocardiogram (ECG) signals from the heart of the patient. Each sensing electrode of the at least two first sensing electrodes has a first recovery time. The first ECG signals may be indicative of an arrhythmia condition of the patient.

The at least two second sensing electrodes are distinct from the at least one therapy electrode and from the at least two first sensing electrodes. The at least two second sensing electrodes are configured to couple externally to the skin of the patient to acquire second ECG signals from the heart of the patient during execution of the treatment protocol. Each sensing electrode of the at least two second sensing electrodes has a second recovery time that is less than the first recovery time. The second ECG signals may be indicative of a reaction of the heart to the one or more therapeutic stimulation pulses.

The at least one processor is coupled to the at least one therapy electrode, the at least two first sensing electrodes, and the at least two second sensing electrodes. The at least one processor is configured to detect the arrhythmia condition via the first ECG signals, to execute the treatment protocol in response to detection of the arrhythmia condition, and to detect the reaction of the heart to the one or more therapeutic stimulation pulses via the second ECG signals.

In the ambulatory medical device, the reaction of the heart may include one or more contractions induced by the one or more therapeutic stimulation pulses. The arrhythmia condition may include at least one of bradycardia, tachycardia, asystole, pulseless electrical activity, atrial flutter, and erratic heart rate. The first recovery time may be an amount of time required for each sensing electrode of the at least two first sensing electrodes to return to a nominal offset after provision of a therapeutic stimulation pulse of the one or more therapeutic stimulation pulses and the second recovery time is an amount of time required for each sensing electrode of the at least two second sensing electrodes to return to a nominal offset after the provision of the therapeutic stimulation pulse. The first recovery time may be between approximately 200 milliseconds and 400 milliseconds and the second recovery time may be between approximately 80 milliseconds and 200 milliseconds. The at least two first sensing electrodes may include dry electrodes and the at least two second sensing electrodes may include conductive electrodes.

The ambulatory medical device may further include a gel dispenser configured to apply conductive gel between the skin of the patient and the at least two second sensing electrodes during execution of the treatment protocol. In the ambulatory medical device, the at least one processor may be further configured to initiate monitoring of the heart of the patient via the at least two second sensing electrodes during execution of the treatment protocol. The ambulatory medical device may further include a therapy pad including the at least one therapy electrode and at least one sensing electrode of the at least two second sensing electrodes. The ambulatory medical device may further include an electrode assembly including at least one sensing electrode of the at least two first sensing electrodes and at least one other sensing electrode of the at least two second sensing electrodes. In the ambulatory medical device, the at least two first sensing electrodes may be physically distinct from the at least two second sensing electrodes.

In another example, an ambulatory medical device is provided. The ambulatory medical device includes at least one therapy electrode, at least two sensing electrodes, circuitry coupled to the at least two sensing electrodes, and at least one processor. The at least one therapy electrode is configured to couple externally to a skin of a patient to provide one or more therapeutic stimulation pulses to a heart of the patient during execution of a treatment protocol. The at least two sensing electrodes are distinct from the at least one therapy electrode and are configured to couple externally to the skin of the patient to acquire first and second electrocardiogram (ECG) signals from the heart of the patient. The first ECG signals may be indicative of an arrhythmia condition of the patient. The second ECG signals may be indicative of a reaction of the heart to the one or more therapeutic stimulation pulses.

The circuitry is configured to transmit the first ECG signals via a first channel and to transmit the second ECG signals via a second channel distinct from the first channel. The at least one processor is coupled to the circuitry, the at least one therapy electrode, and the at least two sensing electrodes. The at least one processor is configured to receive the first ECG signals via the first channel, to detect the arrhythmia condition via the first ECG signals, to execute the treatment protocol in response to detection of the arrhythmia condition, to receive the second ECG signals via the second channel, and to detect the reaction of the heart to the one or more therapeutic stimulation pulses via the second ECG signals.

In the ambulatory medical device, the reaction of the heart may indicate one or more contractions induced by the one or more therapeutic stimulation pulses. The first channel may be a high gain channel and the second channel may be a low gain channel. The high gain channel may amplify the first ECG signal by 150-250 and the low gain channel may amplify the second ECG signal by 1-10.

In another example, an ambulatory medical device is provided. The ambulatory medical device includes a plurality of therapy electrodes, at least two first sensing electrodes, at least two second sensing electrodes, and at least one processor. The plurality of therapy electrodes is configured to couple externally to a skin of a patient at opposite ends of a current path through a heart of the patient to provide one or more therapeutic stimulation pulses to a heart of the patient via the current path during execution of a treatment protocol. The at least two first sensing electrodes are distinct from the plurality of therapy electrodes and are configured to couple externally to the skin of the patient to acquire first electrocardiogram (ECG) signals from the heart of the patient. Each sensing electrode of the at least two first sensing electrodes has a first recovery time. The first ECG signals may be indicative of an arrhythmia condition of the patient.

The at least two second sensing electrodes are distinct from the plurality of therapy electrodes and from the at least two first sensing electrodes. The at least two sensing electrodes are configured to couple externally to the skin of the patient to acquire second ECG signals from the heart of the patient during execution of the treatment protocol. Each sensing electrode of the at least two second sensing electrodes has a second recovery time that is less than the first recovery time. The second ECG signals may be indicative of a reaction of the heart to the one or more therapeutic stimulation pulses. The at least two second sensing electrodes being positioned on a line orthogonal to the current path.

The at least one processor is coupled to the plurality of therapy electrodes, the at least two first sensing electrodes, and the at least two second sensing electrodes. The at least one processor is configured to detect the arrhythmia condition via the first ECG signals, to execute the treatment protocol in response to detection of the arrhythmia condition, and to detect the reaction of the heart to the one or more therapeutic stimulation pulses via the second ECG signals.

In the ambulatory medical device, the reaction of the heart may indicate one or more contractions induced by the one or more therapeutic stimulation pulses. The at least two first sensing electrodes may include dry electrodes and the at least two second sensing electrodes may include conductive electrodes. The ambulatory medical may further include a gel dispenser configured to apply conductive gel between the skin of the patient and the at least two second sensing electrodes during execution of the treatment protocol. In the ambulatory medical device, each sensing electrode of the at least two sensing electrodes may be positioned substantially equidistant from at least one therapy electrode of the plurality of therapy electrodes. The line orthogonal to the current path may substantially bisects the current path. The ambulatory medical device may further include a garment including a plurality of fasteners at predefined locations, wherein the plurality of therapy electrodes, the at least two first sensing electrodes, and the at least two second sensing electrodes are configured to attached to the plurality of fasteners.

In another example, an electrode arrangement is provided. The electrode arrangement includes at least one therapy electrode, at least two dry sensing electrodes, and at least two conductive sensing electrodes. The at least one therapy electrode is configured to couple externally to a skin of a patient to provide one or more therapeutic stimulation pulses to a heart of the patient during execution of a treatment protocol. The at least two dry sensing electrodes are distinct from the at least one therapy electrode and are configured to couple externally to the skin of the patient to acquire first electrocardiogram (ECG) signals from the heart of the patient. Each sensing electrode of the at least two dry sensing electrodes has a first recovery time. The first ECG signals may be indicative of an arrhythmia condition of the patient.

The at least two conductive sensing electrodes are distinct from the at least one therapy electrode and from the at least two dry sensing electrodes. The at least two conductive sensing electrodes are configured to couple externally to the skin of the patient to acquire second ECG signals from the heart of the patient during execution of the treatment protocol. Each sensing electrode of the at least two conductive sensing electrodes has a second recovery time that is less than the first recovery time. The second ECG signals may be indicative of a reaction of the heart to the one or more therapeutic stimulation pulses. In the electrode arrangement, the at least one therapy electrode, the at least two dry sensing electrodes, and the at least two conductive sensing electrodes may be disposed within a garment.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 7 depicts recovery time values in accordance with at least one example disclosed herein.

DETAILED DESCRIPTION

General Overview

Figure 1:
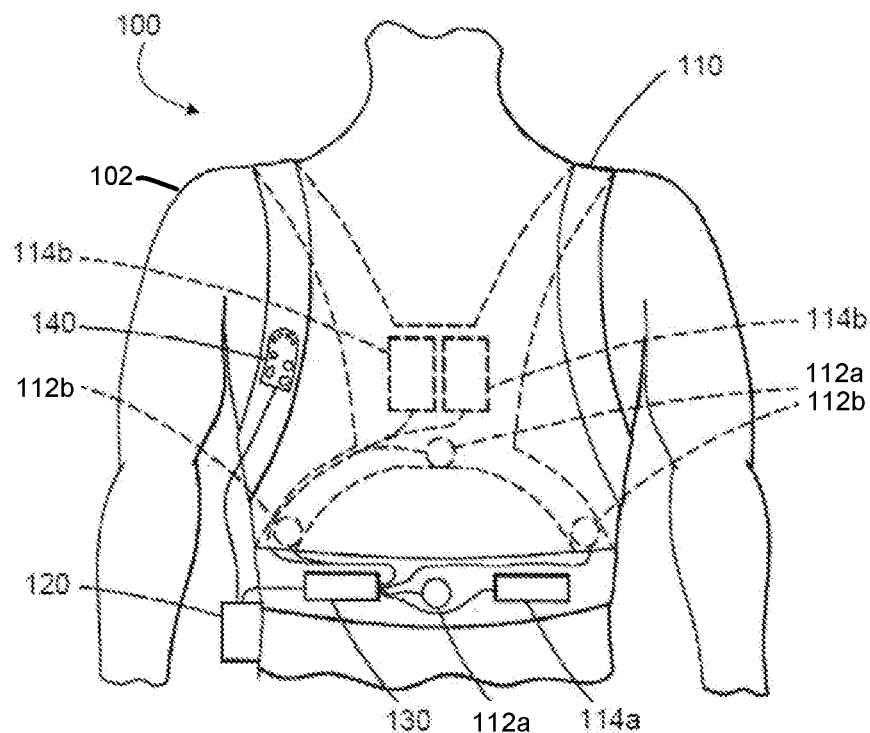
FIG. 1 depicts a wearable, ambulatory, external medical device in accordance with at least one example disclosed herein.

Transcutaneous pacing, which is also referred to as external pacing, is a temporary approach to pacing a patient's heart during a medical emergency using external therapy electrodes. Transcutaneous pacing may be accomplished by delivering pulses of electric energy through the patient's chest via the therapy electrodes. These pulses of electric energy stimulate the heart to contract.

Transcutaneous pacing may be used to treat bradycardia, which is an abnormally slow heart rate. Examples of bradycardia may be less than 40-60 beats per minute. Typically, when bradycardia presents in a patient with a history of cardiac health symptoms, emergency treatment with transcutaneous pacing is required. Some common causes of hemodynamically significant bradycardia include myocardial infarction, sinus node dysfunction, and complete heart block. Another condition that may requirement pacing therapy is tachycardia, a condition typically characterized by an abnormally fast heart rate, e.g., greater than 100 beats per minute in adults.

Therapy electrodes that deliver the electric energy to the patient during pacing are positioned about the patient's chest, e.g., in an anterior/lateral position or an anterior/posterior position. During pacing, a preferred heart rate, e.g., a physician prescribed rate, is selected. Further, a preferred amount of electric current, e.g., selected to be in a range of 25-200 mA (for a selected duration of between about 2 ms to about 80 ms) is set, which is then increased in small increments until capture is detected. For example, capture can occur when the pacing stimulus leads to a reaction of the patient's heart to the electrical stimulus, e.g., a depolarization of the heart ventricles. Such a reaction can be detected via electrocardiogram (ECG) sensors as a widening of the QRS complex and/or T wave morphology changes following a corresponding pacing pulse. For example, the deflection of the captured complex may be positive or negative. A processor in a medical device coupled to the therapy electrodes may acquire ECG signals and monitor the ECG signals for an indication of capture, e.g., monitor for, following an electrical pacing pulse, a widening of the QRS complex over a threshold amount and/or changes in T wave morphology that transgresses predetermined thresholds.

As described above, during pacing, large electrical currents relative to the patient's intrinsic ECG signals are transmitted across the patient's chest to the heart. These momentary currents can saturate the ECG sensing circuitry for a period of time (e.g., between 2 ms to about 100 ms), and consequently obscure the presence of useful ECG activity including indications of capture. For example, arrhythmia monitoring and detection circuits may be designed to monitor for ECG signals that are in the range of around 50 µV to around 5 mV, while pacing transients can create high voltages of around 700 mV or more (even in the presence of clamping diodes that limit the range of input voltage). This disclosure relates to techniques that decrease the time needed for a medical device to recover sensory function subsequent to one or more sensors of the medical device encountering electrical energy not intrinsically generated by a patient, such as a pacing transient. These techniques may be employed, for instance, by medical devices that acquire, analyze, and interpret ECG signals generated by a patient's cardiac function. More specifically, such medical devices may include, as sensors, one or more sensing electrodes that acquire ECG signals from the patient's skin, and circuitry that conditions and converts the acquired ECG signals to ECG data. These medical devices may further include one or more processors that process the ECG data to monitor the patient's cardiac function.

As noted above, ECG data generated from ECG signals acquired in or near the presence of electrical energy not intrinsically generated by the patient may include artifact that obscures the actual ECG signal. For example, such electrical energy may include therapeutic stimulation pulses (e.g., defibrillation, cardioversion, or pacing pulses). Electrical energy of this nature may saturate ECG acquisition circuitry. While the electrodes and circuitry will recover, the time required to do so (e.g., 80 ms-250 ms) may be substantial in view of the duration (e.g., 80-120 ms) of a QRS wave indicative of capture. Consequently, therapeutic stimulation pulses present a problem for the sensory and monitoring functions of medical devices. Some examples disclosed herein address these and other problems.

To enable rapid recovery of sensory function, some examples disclosed herein include sensing electrodes with different recovery times. In some implementations, a medical device uses a first set of electrodes to initially detect an arrhythmia treatable by pacing (e.g., some forms of bradycardia and tachycardia) and uses a second set of electrodes to detect the reaction of a patient's heart to the pacing pulses (e.g. detecting capture). In these example, the first set of electrodes and associated circuitry are configured to have a longer recovery time than the second set of electrodes and its associated circuitry, but the first set of electrodes are suitable for long-term continuous use that is comfortable for the patient, while the second set may not be not suitable for long-term continuous use. By utilizing the second set of electrodes only for limited periods of time (e.g., when rapid recovery from saturation is most needed such as when monitoring for capture during pacing), these examples decrease the recovery time required by the sensory functions of the medical device when compared to medical devices that employ only electrodes suitable for long-term continuous use.

To recover sensory function rapidly, some examples monitor a patient's cardiac function by referring to data generated by one of two or more distinctly conditioned signals. For instance, in several examples, during times other than a limited period near the provision of therapeutic stimulation pulses, a medical device monitors the patient's cardiac function with reference to a first signal channel or mode conditioned by a first circuit. In these examples, during times within the limited period near the provision of the therapeutic stimulation pulses, the medical device monitors the reaction of the patient's heart to the therapeutic stimulation pulses with reference to a signal channel or mode conditioned by a second circuit. By utilizing conditioning circuitry that is tailored to the environment in which the signals are acquired, medical devices in accord with these examples recover sensory functions more quickly than medical devices that condition all signals via the same circuitry. Further, the medical devices described herein can dynamically switch between the first circuit and second circuit depending on the context.

To enable rapid recovery of sensory function, some examples disclosed herein include electrodes disposed in specific locations relative to known artifact generators. For instance, in several examples, a medical device uses a set of electrodes that are positioned orthogonally to a path traversed by therapeutic stimulation pulses. By being disposed in these locations, the set of electrodes encounters less artifact and, therefore, requires less time to recover than sets of electrodes positioned less advantageously.

In some examples, an arrangement of electrodes, such as any of those described above, may be provided for attachment to a patient so that a medical device connected to the arrangement may benefit from rapid recover times. In several such examples, the arrangement is embedded within a garment that, when properly fitted to the patient, disposes, orients, and attaches each of the electrodes in the arrangement to the patient. These and other examples will become apparent to one of ordinary skill in light of the present disclosure.

Therapeutic stimulation pulses are disruptive to the sensory functions of medical devices due to the amount of energy such pulses transfer to the patient's body and the medical devices' sensors and circuitry relative to intrinsically generated patient signals such as ECG signals. For example, normal ECG signals include a peak amplitude of approximately 3 millivolts. In contrast, transcutaneous defibrillation pulses may impart from 60 to 400 joules of energy and transcutaneous pacing pulses may impart from 10-250 milliamps (approximately 0.5-500 millijoules, depending on patient impedance). When exposed to pulses with these characteristics, conventional medical devices require substantial time to recovery their sensory function. For example, medical devices employing conventional dry electrodes may take anywhere from about 150 ms to about 500 ms to return to a baseline state after encountering a therapeutic electrical pulse. The medical device's inability to monitor a patient during this period of time can adversely impact patient care. For example, an external pacing device may be unable to initially determine whether a pacing pulse resulted in capture of the patient's heart due to a slow recovery time.

Thus, and in accordance with the various examples disclosed herein, techniques and apparatus for decreasing recovery time are provided. These techniques and apparatus enable medical devices to recover sensory function faster than conventional medical devices. Faster sensory recovery, in turn, enables these medical devices to monitor patients more comprehensively and, in some examples, treat patients more efficiently. For instance, pacing medical devices that incorporate the techniques and apparatus disclosed herein are able to determine whether pacing pulses result in capture (e.g., whether myocardial depolarization occurs in response pacing pulses). Similarly, monitoring medical devices that incorporate the techniques and apparatus disclosed herein are able to record and transmit a more complete account of a patient's cardiac activity. These and other functions of medical devices can be enhanced using the techniques and apparatus disclosed herein.

Example Medical Devices

The teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device is capable of continuous (e.g., substantially or nearly continuous) use by the patient. In some implementations, the continuous use may be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, heart sounds, etc.) and/or non-cardiac information (e.g., blood oxygen, the patient's temperature, glucose levels, tissue fluid levels, and/or lung sounds). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung sounds (e.g., using microphones and/or accelerometers), breath sounds, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's electrocardiogram (ECG) information, heart sounds (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart sounds (e.g., using accelerometers or microphones), lung sounds, breath sounds, sleep related parameters (e.g., snoring, sleep apnea), tissue fluids, among others.

FIG. 1 illustrates an example medical device 100 that is external, ambulatory, and wearable by a patient 102, and configured to use one or more of the techniques described herein to rapidly recover sensory function after the patient 102 receives a therapeutic electrical pulse. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic stimulation pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., anterior/posterior ECG electrodes 112a and side/side ECG electrodes 112b), one or more therapy electrodes 114 (e.g. anterior therapy electrode 114a and posterior electrodes 114b), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. One such configuration, which decreases recovery time for the sensory functions of the medical device 100, is described further below with reference to FIG. 12. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

Example sensing electrodes 112 can include dry electrodes or conductive electrodes as described in further detail below. In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device 100.

WMD/WCD Controller Description

Figure 2:
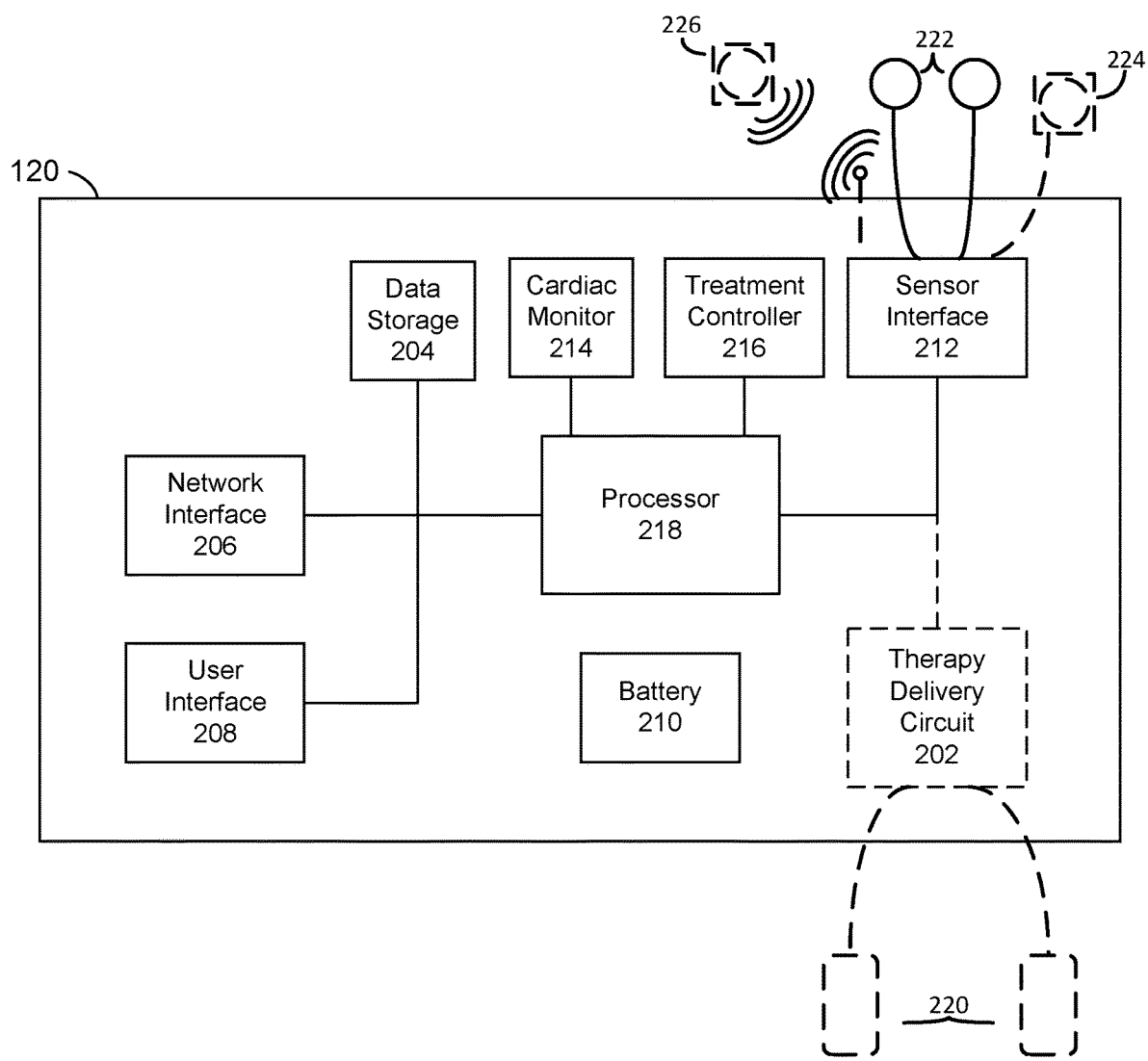
FIG. 2 depicts an arrangement of components of a medical device controller in accordance with at least one example disclosed herein.

FIG. 2 illustrates a sample component-level view of the medical device controller 120. As shown in FIG. 2, the medical device controller 120 can include a therapy delivery circuit 202, a data storage 204, a network interface 206, a user interface 208, at least one battery 210, a sensor interface 212, a cardiac monitor 214, a treatment controller 216, and at least one processor 218. A patient monitoring medical device can include a medical device controller 120 that includes like components as those described above, but does not include the therapy delivery circuit 202 (shown in dotted lines).

The therapy delivery circuit 202 can be coupled to one or more electrodes 220 configured to provide therapy to the patient (e.g., therapy electrodes 114a-b as described above in connection with FIG. 1). For example, the therapy delivery circuit 202 can include, or be operably connected to, circuitry components that are configured to generate and provide the therapeutic electrical pulse or shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack, such as the at least one battery 210.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device.

In certain implementations, the user interface 208 can include one or more physical interface devices such as input devices, output devices, and combination input/output devices and a software stack configured to drive operation of the devices. These user interface elements may render visual, audio, and/or tactile content, including content relating to location-specific processing. Thus the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1), heart sounds sensors 224, and tissue fluid monitors 226 (e.g., based on ultra-wide band radiofrequency devices). As such, the sensor interface 212 may include amplifiers and analog to digital converters to condition and digitize signals acquired by the sensors.

The ECG electrodes 222 can monitor a patient's ECG information. For example, the ECG electrodes 222 can be conductive and/or dry electrodes configured to measure changes in a patient's electrophysiology to measure the patient's ECG information. The ECG electrodes 222 can transmit information descriptive of the ECG signals to the sensor interface 212 for subsequent analysis.

The heart sounds sensors 224 can detect a patient's heart sound information. For example, the heart sounds sensors 224 can be configured to detect heart sound values including any one or all of S1, S2, S3, and S4. From these heart sound values, certain heart sound metrics may be calculated, including any one or more of electromechanical activation time (EMAT), percentage of EMAT (% EMAT), systolic dysfunction index (SDI), and left ventricular systolic time (LVST). The heart sounds sensors 224 can include an acoustic sensor configured to detect sounds from a subject's cardiac system and provide an output signal responsive to the detected heart sounds. The heart sounds sensors 224 can also include a multi-channel accelerometer, for example, a three channel accelerometer configured to sense movement in each of three orthogonal axes such that patient movement/body position can be detected and correlated to detected heart sounds information. The heart sounds sensors 224 can transmit information descriptive of the heart sounds information to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by heart sounds sensor 224 and transmitted to the sensor interface 212, the sensor interface 212 can transmit the data to the processor 218 which, in turn, relays the data to the cardiac monitor 214 and/or the treatment controller 216. This data can also be stored on the data storage 204.

According to some examples illustrated by FIG. 2, the cardiac monitor 214 is configured to initiate and control monitoring of a patient's cardiac function and identification of arrhythmias experienced by the patient. When executing according to this configuration, in some examples, the cardiac monitor 214 detects arrhythmias by scanning ECG data received from the sensor interface 212 for patterns (e.g. heart rates) indicative of arrhythmias. Responsive to identifying a data pattern indicative of an arrhythmia, the cardiac monitor 214 initiates the treatment controller 216. According to various examples, to identify arrhythmias, the cardiac monitor 214 executes sub-processes that are specific to one or more rapid recovery techniques implemented in the example. Examples of these sub-processes are described further below with reference to FIGS. 3, 5, and 8.

According to some examples illustrated by FIG. 2, the treatment controller 216 is configured to initiate and control treatment of an arrhythmia identified by the cardiac monitor 214. When executing according to this configuration, in some examples, the treatment controller 216 executes a treatment protocol specific to the particular identified arrhythmia. For instance, the treatment controller 216 may pace a patient experiencing bradycardia or ventricular tachycardia or may defibrillate a patient experiencing atrial or ventricular fibrillation. In some examples, the treatment controller 216 initiates deployment of electrically conductive gel as part of the treatment protocol. Also, in some examples, the treatment controller 216 monitors the reaction of the patient's heart to the treatment protocol and takes further action based on the reaction of the patient's heart. This further action may include altering the treatment protocol and/or escalating notifications to external parties. According to various examples, to treat arrhythmias, the treatment controller 216 executes sub-processes that are specific to one or more rapid recovery techniques implemented in the example. Examples of these sub-processes are described further below with reference to FIGS. 3, 5, and 8.

In some examples, the treatment controller 216 is configured to execute one or more software filters that decrease artifacts present in ECG signals acquired by electrodes that have not fully recovered from a therapeutic stimulation pulse. Without such filtering, the polarization artifact may adversely affect analysis of the ECG signals for the entire recovery time period. However, with the software filtering in place, the ECG signals can be satisfactory analyzed starting at approximately 80-150 milliseconds after provision of the therapeutic stimulation pulse, depending on the type of electrode used to acquire the ECG signals (e.g., with conductive electrodes being at the lower end of this range).

Both the cardiac monitor 214 and the treatment controller 216 can be implemented using hardware or a combination of hardware and software. For instance, in some examples, the cardiac monitor 214 and/or the treatment controller 216 are implemented as software components that are stored within the data storage 204 and executed by the processor 218. In this example, the instructions included in the cardiac monitor 214 and/or the treatment controller 216 can cause the processor 218 to monitor for, detect, and treat arrhythmias. In other examples, the cardiac monitor 214 and/or the treatment controller 216 are application-specific integrated circuits (ASICs) that are coupled to the processor 218 and configured to monitor for, detect, and treat arrhythmias. Thus, examples the cardiac monitor 214 and the treatment controller 216 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring, treatment, etc.), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

Overview of Various Rapid Recovery Features

Medical devices in accord with various examples disclosed herein utilize one or more of a variety of features to recover sensory functions more rapidly than conventional medical devices. Prior to describing each of these features in detail, a brief overview will be provided for each.

A first set of examples can be described with combined reference to FIGS. 1 and 2. These examples are configured to advantageously leverage differences between a first type of sensing electrode and a second type of sensing electrode that has a shorter recovery time than the first type of sensing electrode. When executing according to these configurations in some examples, a medical device (e.g., the medical device 100) operates in a monitoring mode and/or a treatment mode. In monitoring mode, the medical device acquires and processes ECG signals using components suitable for long term patient monitoring. In treatment mode, the medical device acquires and processes ECG signal using components suitable for short term patient treatment (e.g., via pacing). As described further below, the components used in the treatment mode have substantially faster recovery times than those used in the monitoring mode.

More specifically, when operating in the monitoring mode, the medical device uses one or more sensing electrodes of the first type (e.g. side/side electrodes 112b) to acquire ECG signals from a patient's (e.g., the patient 102) heart. Also, while operating in the monitoring mode, at least one processor (e.g., the at least one processor 218) of the medical device receives, from a sensor interface (e.g., the sensor interface 212), processed ECG data representative of the acquired ECG signals. The at least one processor provides the ECG data to a cardiac monitor (e.g., the cardiac monitor 214). The cardiac monitor processes the ECG data to monitor the patient's cardiac function. Should the cardiac monitor indicate that the patient is experiencing an arrhythmia condition (e.g., bradycardia, tachycardia, asystole, pulseless electrical activity, atrial flutter, or erratic heart rate), the medical device shifts into the treatment mode.

When operating in the treatment mode, the medical device uses one or more sensing electrodes of the second type (e.g., anterior/posterior electrodes 112a) to acquire ECG signals from the patient's heart. Also, while operating in the treatment mode, the at least one processor receives, from the sensor interface, processed ECG data representative of these acquired ECG signals. The at least one processor provides the ECG data to a treatment controller (e.g., the treatment controller 216). The treatment controller executes a treatment protocol in which at least one therapy electrode (e.g., the therapy electrodes 114) of the medical device provides one or more therapeutic stimulation pulses to the patient's heart. Also, within the treatment mode, the treatment controller monitors the patient's heart via the ECG data for a reaction to the one or more therapeutic stimulation pulses. This reaction may include, for example, one or more contractions induced by the therapeutic stimulation pulses.

In some examples, the first type of sensing electrodes includes dry electrodes, and the second type of sensing electrodes includes conductive electrodes. In an implementation, a dry electrode can include a metal substrate with an oxide coating deposited on the substrate. For example, such a dry electrode can include tantalum—tantalum pentoxide electrodes, as described in, for example, U.S. Pat. No. 6,253,099 titled "Cardiac Monitoring Electrode Apparatus and Method," which is hereby incorporated herein by reference in its entirety. For example, a dry electrode can be constructed by forming a tantalum metal substrate, and depositing a tantalum pentoxide layer on the metal surface. An anodizing process can be used to form the oxide layer. The oxide layer can cover an entire surface of the metal substrate including the outer edges. Such a dry electrode can be placed directly on a patient's skin to acquire ECG signals without the presence of an electrolyte. A dry electrode can be regarded as having characteristics close to a polarizable electrode, for example, because no actual charge transfers across the electrode interface. In this sense, a dry electrode behaves like a capacitor where it can be regarded as sensing displacement current across the electrode interface rather than actual charge transfer across the interface.

In certain examples, a conductive electrode can include a foundational layer (e.g., made of foam), an electrically conductive element (e.g., made of tin, silver-silver chloride, etc.), and an electrolytic gel layer (e.g., made of hydrogel) that electrically couples the conductive element to the patient's skin. This electrolytic layer may be applied manually by a healthcare provider or may be disposed automatically by a gel dispenser positioned near the conductive electrode. A conductive electrode can be regarded as having characteristics close to a non-polarizable electrode, for example, because the conductive electrode senses actual charge transfer or current that passes across the electrode-electrolytic interface based on ionic conduction on the patient's skin.

Because conductive electrodes in operation behave more like resistors, they tend to have a shorter or faster recovery time than dry electrodes, which behave like leaky capacitors. More specifically, dry electrodes generally have a recovery time of between approximately 150 milliseconds and approximately 400 milliseconds, where the recovery time includes an amount of time required for the sensing electrodes and/or associated ECG circuitry to return to a baseline level after encountering a saturating signal. In contrast, conductive electrodes generally have a recovery time between approximately 80 milliseconds and 200 milliseconds.

A saturating signal as described herein can be an electrical pulse, such as a defibrillation or pacing pulse, that is applied by an external electrode and that appears as a differential signal between two sensing electrodes. As such, the power of a saturating signal is generally outside the range of typical patient generated ECG signals. To prevent a saturating signal from disrupting ECG signal acquisition, some example medical devices disclosed herein are configured to implement a blanking interval. During a blanking interval, ECG signal acquisition circuitry is disconnected from sensing electrodes and/or ECG signals acquired are ignored. The timing and duration of a blanking interval may be based on the time that a therapeutic electrical pulse is issued and the recovery time of the type of sensing electrode being used to detect ECG signals. Once example of switch circuitry that is configured to implement a blanking interval is described further below with reference to FIG. 13.

In some examples, the conductive electrodes may be included in an electrode assembly that further includes a gel dispenser under the control of the treatment controller. The gel dispenser may house and deploy electrically conductive gel to increase the quality of the electrical connection between the conductive electrode and the skin of the patient should pacing and/or defibrillation be needed. In some examples, the gel dispenser and the conductive electrodes are incorporated into a therapy pad that includes the therapy electrodes. In other examples, the conductive electrodes are incorporated into an electrode assembly with at least one dry electrode. In still other examples, the conductive electrodes and the dry electrodes are housed within physically distinct electrode assemblies. These and other features of these examples are described further below with reference to FIGS. 3-7.

While the first set of examples leverage differences in recovery times of different types of sensing electrodes to decrease recovery time of medical device functionality, a second set of examples alternatively or additionally leverage distinct processing modes to a similar effect. For instance, as described further below with reference to FIGS. 8-10, some examples of the medical device, the sensor interface 212 includes circuitry configured to condition acquired ECG signals via two or more distinct processing modes. For example, the two or more distinct processing modes may be implemented by providing two or more distinct circuit paths or channels for processing each ECG signal from the patient. Accordingly, the at least one processor can be configured to refer to ECG data conditioned via these distinct circuits when monitoring and treating the patient. A first circuit path of the two or more distinct circuit paths may be configured to condition signals acquired during a cardiac monitoring period when the device is monitoring the patient's ECG for cardiac arrhythmias. A second circuit path, on the other hand, may be configured to condition signals acquired during a treatment period near and subsequent to (e.g., within approximately 200 ms or more, depending on circuit design) the provision of one or more therapeutic stimulation pulses by the therapy electrode. For example, the first circuit path or channel may include high gain circuit elements configured to amplify acquired electrical signals sensed by the ECG electrodes 222 by a gain in a range of, e.g., 100-1000. The second circuit or channel may include low gain circuit elements (e.g., amplifiers with a lower gain relative to amplifiers used in the first circuit path) and configured to amplify electrical signals also sensed by the ECG electrodes 222 by a gain in a range of, e.g., 10-500. Depending on circuit design and configuration, other gain values are possible. It is understood, however, that the second circuit for detecting and monitoring pacing capture is configured with lower gain circuit elements in order to speed up circuit recovery following a saturating pacing transient. Additional circuits with varying gains are possible. In operation, the processor can dynamically switch between the different circuits to determine an appropriate gain setting to determine capture. For example, the processor can have a default gain setting for arrhythmia monitoring, and switch to other gain modes or channels during a treatment period to identify evidence of capture. These and other features of these examples are described further below with reference to FIGS. 8-10.

A third set of examples arrange sensing electrodes and therapy electrodes in a specific layout to enable rapid recovery of medical device sensory functionality. For example, with reference to FIGS. 1 and 2, in some examples of the medical device the sensing electrodes and therapy electrodes are arranged in a specific layout that minimizes the amount of energy imparted by the therapy electrodes that is encountered by the sensing electrodes. In some of these examples, the layout of the electrodes specifies that the therapy electrodes be positioned at opposite ends of a current path that intersects the patient's heart. The layout also specifies that the sensing electrodes be positioned along a line orthogonal to the current path. The layout may further specify that the line orthogonal to the current path bisects the current path and/or that each sensing electrode be positioned equidistant from a therapy electrode. Positioned thusly, the sensing electrodes are more likely to encounter less artifact from the one or more therapeutic stimulation pulses provided by the therapy electrodes. In some examples, the layout is embedded within a garment (e.g., the garment 110). Further, in some examples, the sensing electrodes include a first type of sensing electrode and a second type of sensing electrode that has a shorter recovery time than the first type of sensing electrode. The first type of sensing electrode may include dry electrodes, and the second type of sensing electrode may include conductive electrodes. These first and second types of sensing electrodes may be used by the medical device to monitor the patient, when executing in a monitoring mode, and treat the patient, when executing in a treatment mode, as described above. These and other features of these examples are described further below with reference to FIGS. 11 and 12.

Example Implementations

Some examples enable rapid recovery of sensory function by leveraging differences in recovery times between different types of sensing electrodes. In some of these examples, the cardiac monitor and the treatment controller described above with reference to FIG. 2 are configured to utilize different types of sensing electrodes within a monitoring and treatment process as illustrated in FIG. 3.

Figure 3:
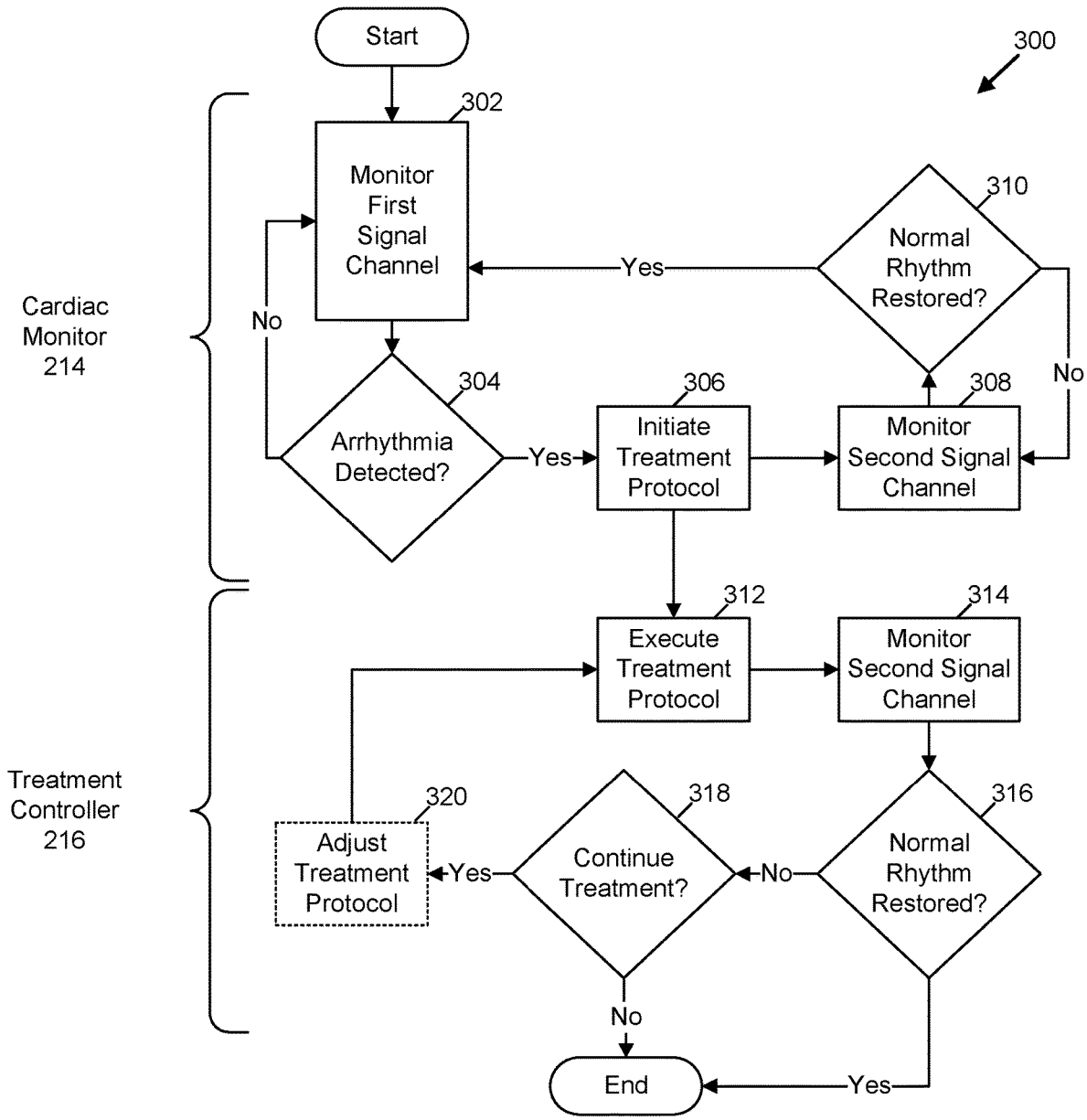
FIG. 3 depicts a monitoring and treatment process in accordance with at least one example disclosed herein.

More specifically, FIG. 3 depicts a monitoring and treatment process 300 executed jointly by the cardiac monitor and the treatment controller. The monitoring and treatment process 300 starts in the act 302 with the cardiac monitor monitoring ECG data received via a first signal channel. In some examples, the circuitry that acts as a conduit of this ECG data includes the sensing electrodes of the first type (e.g., conductive electrodes) and the sensor interface. In act 304, the cardiac monitor determines whether the ECG data indicates that the patient is experiencing an arrhythmia. If so, the cardiac monitor initiates a treatment protocol in act 306. If the cardiac monitor does not detect an arrhythmia in the act 304, the cardiac monitor returns to the act 302.

In the act 306, the cardiac monitor calls the treatment controller to initiate its execution of the act 312 and proceeds to act 308. In the act 308, the cardiac monitor monitors ECG data received via a second signal channel. In some examples, the circuitry that acts as a conduit of this ECG data includes the sensing electrodes of the second type (e.g., conductive electrodes) and the sensor interface. Because this ECG data is based on ECG signals acquired by the second type of electrodes, which have a shorter recovery time than the first type of electrodes, the at least one processor of the medical device will be able to accurately process the ECG data more quickly than ECG data based on ECG signals acquired by the first type of electrodes. In act 310, the cardiac monitor determines whether the ECG data indicates that the patient's normal cardiac rhythm has been restored. If so, the cardiac monitor returns to the act 302. If the cardiac monitor does not detect restoration of the patient's normal cardiac rhythm in the act 310, the cardiac monitor continues to monitor the second signal channel by returning to the act 308.

Figure 4:
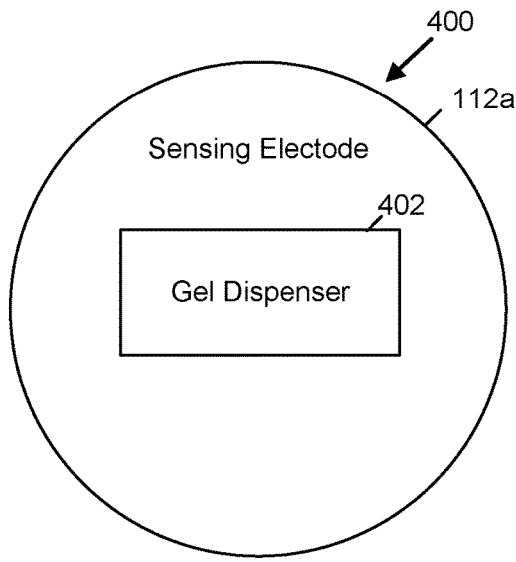
FIG. 4 depicts a sensing electrode in accordance with at least one example disclosed herein.
Figure 5:
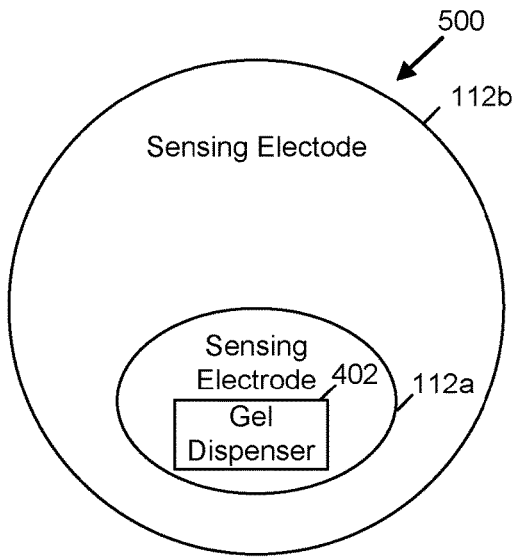
FIG. 5 depicts another sensing electrode in accordance with at least one example disclosed herein.

In the act 312, the treatment controller executes a treatment protocol. When executing this treatment protocol, the treatment controller may coordinate and control various components of the medical device to provide treatment to the patient. For example, the treatment controller may provide one or more therapeutic stimulation pulses, such as pacing pulses and/or defibrillating shocks, to the patient's body via the therapy electrodes. Prior to providing the one or more therapeutic stimulation pulses, in some examples, the treatment controller may signal a gel dispenser housed within an electrode assembly to dispose electrically conductive gel between the skin of the patient and a sensing electrode of the second type. FIGS. 4 and 5, which are described below, illustrate two examples of such an electrode assembly. Similarly, the treatment controller may signal one or more gel dispensers housed in a therapy pad to dispose electrically conductive gel between the skin of the patient and an electrode of the second type, and between the skin of the patient and a therapy electrode.

In act 314, the treatment controller monitors ECG data received via the second signal channel. Because this ECG data is based on ECG signals acquired by the second type of electrodes, which have a shorter recovery time than the first type of electrodes, the at least one processor of the medical device will be able to accurately process the ECG data more quickly than ECG data based on ECG signals acquired by the first type of electrodes. In act 316, the treatment controller determines whether the ECG data indicates that the patient's normal cardiac rhythm has been restored. If so, the treatment controller terminates its portion of the monitoring and treatment process 300. If the treatment controller does not detect restoration of the patient's normal cardiac rhythm in the act 316, the treatment controller proceeds to act 318.

In the act 318, the treatment controller determines whether treatment of the patient should continue. For example, within the act 318, the treatment controller may determine whether execution of the treatment protocol has continued for longer than a threshold duration or for more than a threshold number of cycles. Also, within the act 318, the treatment controller may determine whether the medical device has sufficient resources available to continue execution of the treatment protocol (e.g., whether sufficient battery power remains). If, in the act 318, the treatment controller determines that treatment of the patient should not continue, the treatment controller terminates its portion of the monitoring and treatment process 300. If, in the act 318, the treatment controller determines that treatment of the patient should continue, the treatment controller optionally proceeds to act 320.

In the act 320, the treatment controller determines whether any adjustments to the treatment protocol should be made. For example, within the act 320, the treatment controller may analyze the ECG data received via the second signal channel within the act 314 to determine adjustments to make to the characteristics of therapeutic stimulation pulses provided by the therapy electrode. These characteristics may include level of current, pulse width, pulse rate, and waveform among other characteristics. Adjustments identified with in the act 320 may be based on an inability of the treatment protocol to capture, cardiovert, or defibrillate the patient. In some examples, the treatment controller may be able to make beneficial adjustments to the treatment protocol more quickly than otherwise would be possible due to the early availability of accurate ECG data via the second signal channel. After appropriately adjusting the treatment protocol, the treatment controller returns to the act 312 and continues to treat the patient.

Examples implementing the monitoring and treatment process 300, are able to execute treatment protocols using ECG data that more completely covers the patient's cardiac activity during, and in response to, treatment.

FIG. 4 illustrates one example of an electrode assembly 400 that includes the sensing electrode 112a and a gel dispenser 402. The sensing electrode 112a is a sensing electrode of the second type (i.e., an electrode with a shorter recovery time than conventional dry electrodes) may include, for example, a conductive electrode. As described above with refer to FIG. 1, the sensing electrode 112a may include a foundational layer (e.g., made of foam), an electrically conductive element (e.g., made of tin, silver-silver chloride, etc.), and an electrolytic layer (e.g., made of hydrogel) that electrically couples the conductive element to the patient's skin. In some examples of the electrode assembly 400, the electrolytic layer is established during the treatment protocol and under control of the treatment controller by the gel dispenser 402. The gel dispenser 402 may include, for example, a gel reservoir that is ruptured to dispose the gel between the electrically conductive element and the skin of the patient. As described above, the sensing electrode 112a may acquire ECG signals that are conditioned and processed by the medical device to determine the patient's cardiac condition.

FIG. 5 illustrates another example of an electrode assembly 500 that includes the sensing electrode 112b, the gel dispenser 402, and the sensing electrode 112b. The sensing electrode 112b is a sensing electrode of the first type (i.e., an electrode with the recovery time of conventional dry electrodes) may include, for example, a dry electrode. As described above with refer to FIG. 1, the sensing electrode 112b may include a metal electrode with an oxide coating such as tantalum pentoxide electrodes, as described in, for example, U.S. Pat. No. 6,253,099. In some examples of the electrode assembly 500, the sensing electrode 112a is electrically isolated from the surface of the sensing electrode 112b. As described above, the sensing electrodes 112a and 112b may acquire ECG signals that are conditioned and processed by the medical device to determine the patient's cardiac condition.

Figure 6:
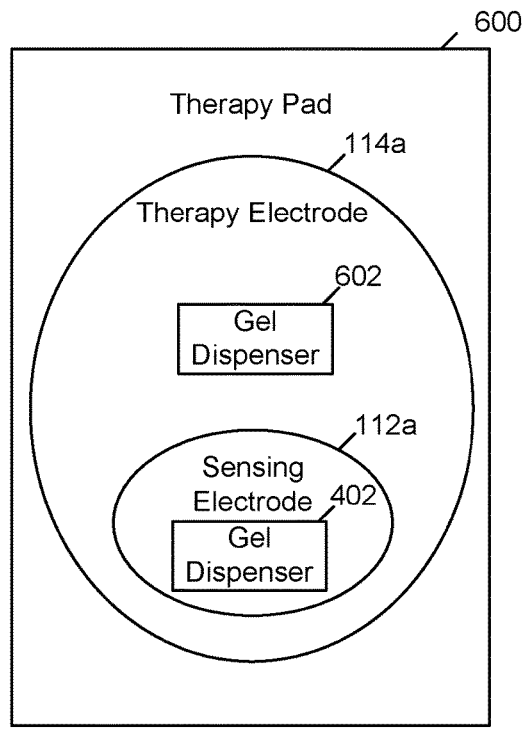
FIG. 6 depicts a therapy pad in accordance with at least one example disclosed herein.

In some examples, the gel may be disposed in a manner that prevents the gel from acting as a direct electrical connection between the therapy electrode and the electrode of the second type. FIG. 6 illustrates one example of such a therapy pad 600 that includes the sensing electrode 112a, the gel dispenser 402, a gel dispenser 602, and the therapy electrode 114a. In some examples of the therapy pad 600, the gel dispenser 602 operates under control of the treatment controller and, during the treatment protocol, disposes a layer of electrically conductive gel between the therapy electrode 114a and the skin of the patient. As described above, the gel dispenser 402 may dispose a layer of electrically conductive gel between the sensing electrode 112a and the skin of the patient. In some examples, the stainless steel layer of the therapy electrode 114a is used as a conductive electrode. In some examples, a portion of the therapy electrode 114a is electrically isolated from the remainder of the therapy electrode 114a and used as the sensing electrode 112a. As described above, the sensing electrode 112a may acquire ECG signals that are conditioned and processed by the medical device to determine the patient's cardiac condition. Also as described above, the therapy electrode 114a may provide one or more therapeutic stimulation pulses to the patient. In some examples, the medical device including the therapy pad 600 is configured to use the therapy electrode 114a as a ground during provision of one or more therapeutic stimulation pulses. In such as configuration the sensing electrode 112a benefits from the fact that the therapy electrode 114a has relatively low voltage during provision of the one or more therapeutic stimulation pulses. This lower voltage, in turn, causes less sensory disruption relative to other configurations.

FIG. 7 is a table listing recovery time data acquired during animal (swine) testing. This testing was conducted with a WCD, such as the model 4000 LifeVest® brand wearable defibrillator, and a hospital wearable defibrillator (HWD), such as the model HWD-1000, both available from ZOLL medical corporation. The WCD included dry electrodes. The HWD included conductive electrodes. During the testing, the animal was anesthetized and given a beta-blocker to establish a heart rate of between 90 and 85 BPM. The WCD was fitted to the animal, conductive gel was dispensed, and the WCD was configured to pace the animal at a rate of 90 BPM. The energy and duration of the pacing pulses used was varied as shown in Table 1. Next, the animal was fitted with the HWD and the HWD was configured to pace the animal at a rate of 85 BPM. The energy and duration of the pacing pulses was varied as shown in Table 1. As illustrated, the ECG signal recovery time was consistently shorter for the HWD when compared to the WCD.

Figure 14:
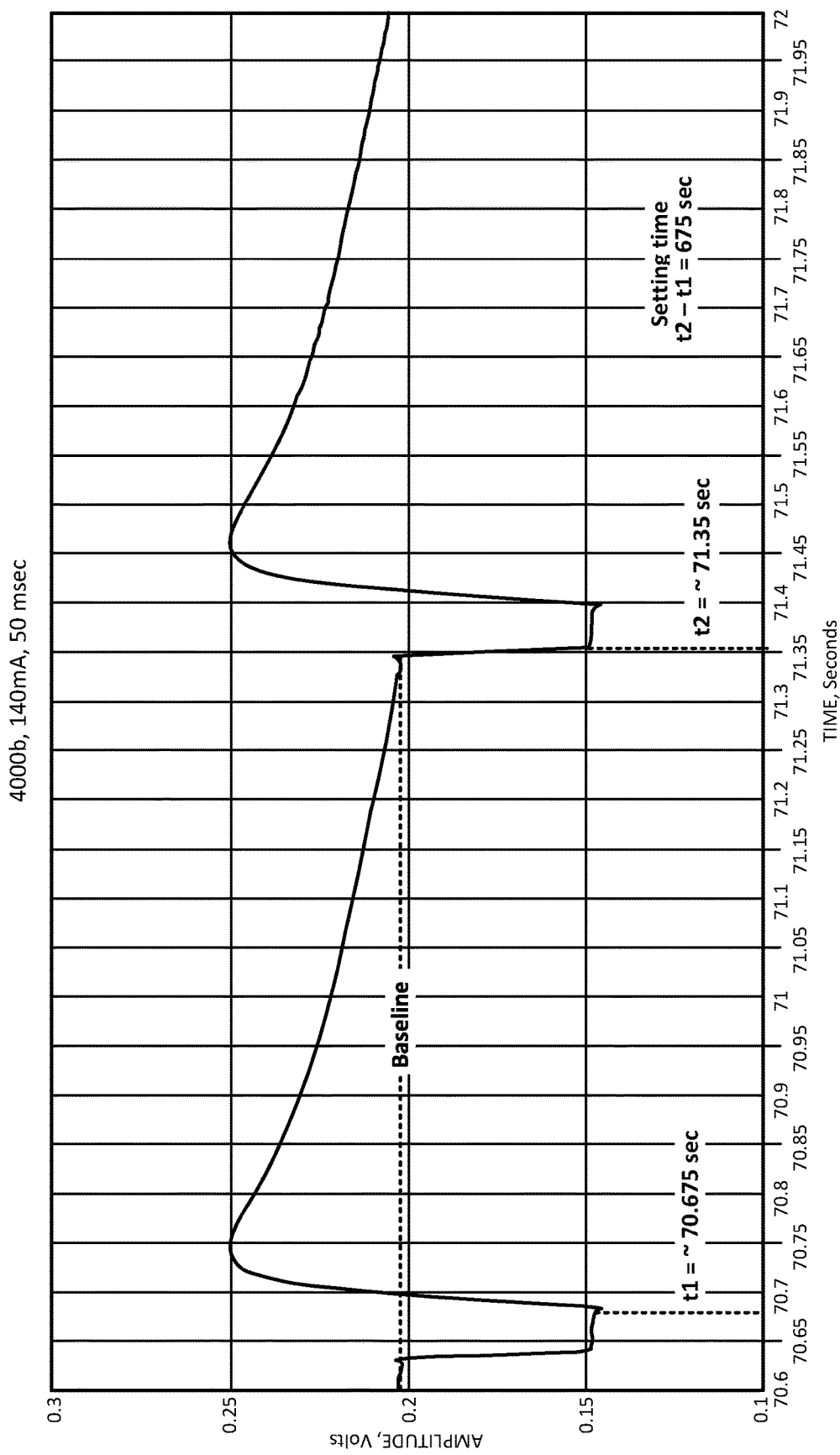
FIG. 14 is a graph illustrating time period required for an electrode to recover after issuance of a therapeutic stimulation pulse in accordance with at least one example disclosed herein.

FIG. 14 is a graph illustrating the time required for a dry electrode to recover after issuance of a therapeutic stimulation pulse. As shown in FIG. 14, the recovery time period (which is referred to as settling time in FIG. 14) is approximately 675 milliseconds and begins at t1 and ends at t2, with the sensed amplitude returning to a nominal, baseline value. The data used to produce the graph of FIG. 14 was collected during the animal test described above with reference to FIG. 7.

Figure 15:
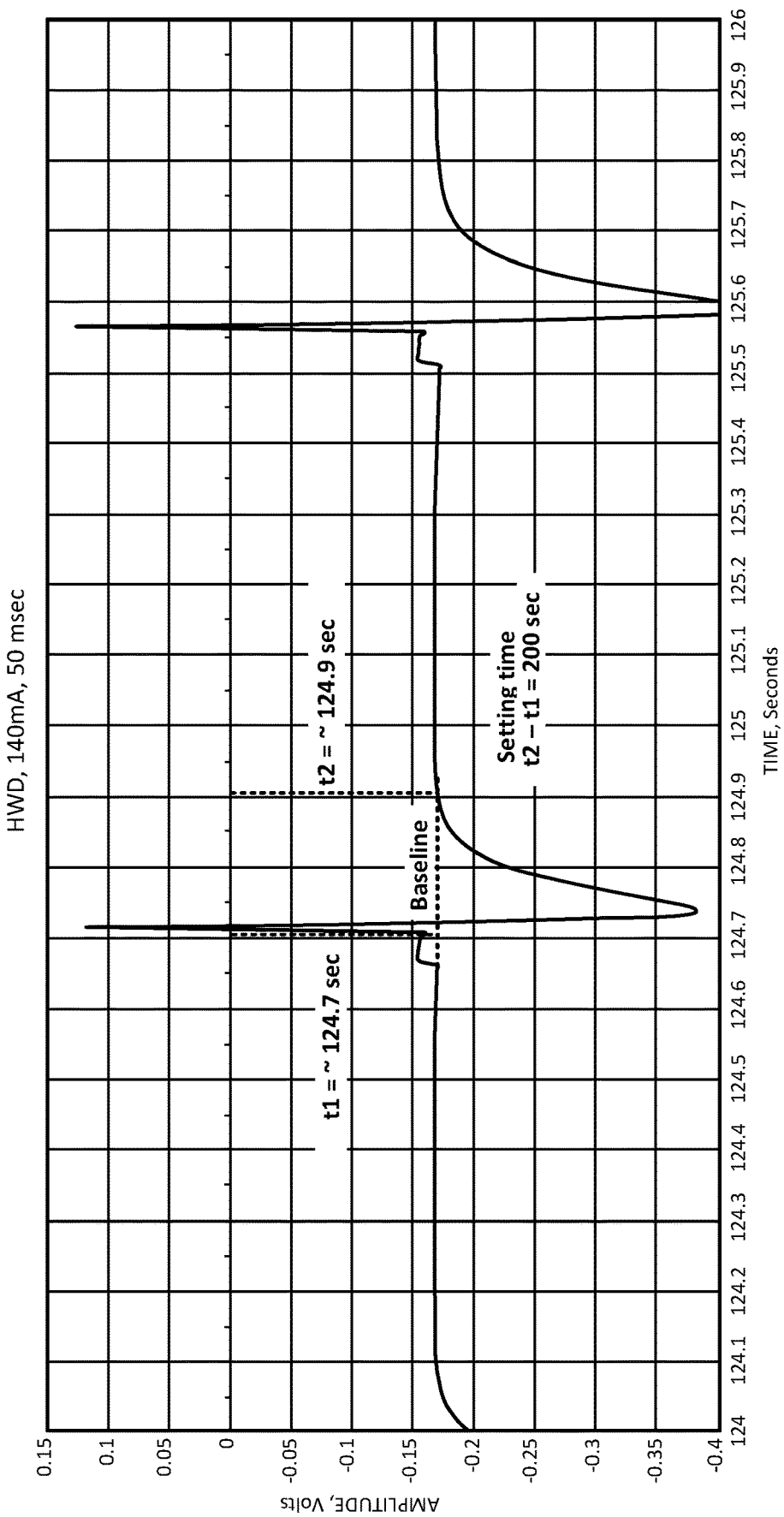
FIG. 15 is another graph illustrating the time required for an electrode to recover after issuance of a therapeutic stimulation pulse in accordance with at least one example disclosed herein.

FIG. 15 is a graph illustrating the time required for a conductive electrode to recover after issuance of a therapeutic stimulation pulse. As shown in FIG. 15, the recovery time period (which is referred to as settling time in FIG. 15) is approximately 200 milliseconds and begins at t1 and ends at t2, with the sensed amplitude returning to a nominal, baseline value. The data used to produce the graph of FIG. 15 was collected during the animal test described above with reference to FIG. 7.

Figure 9:
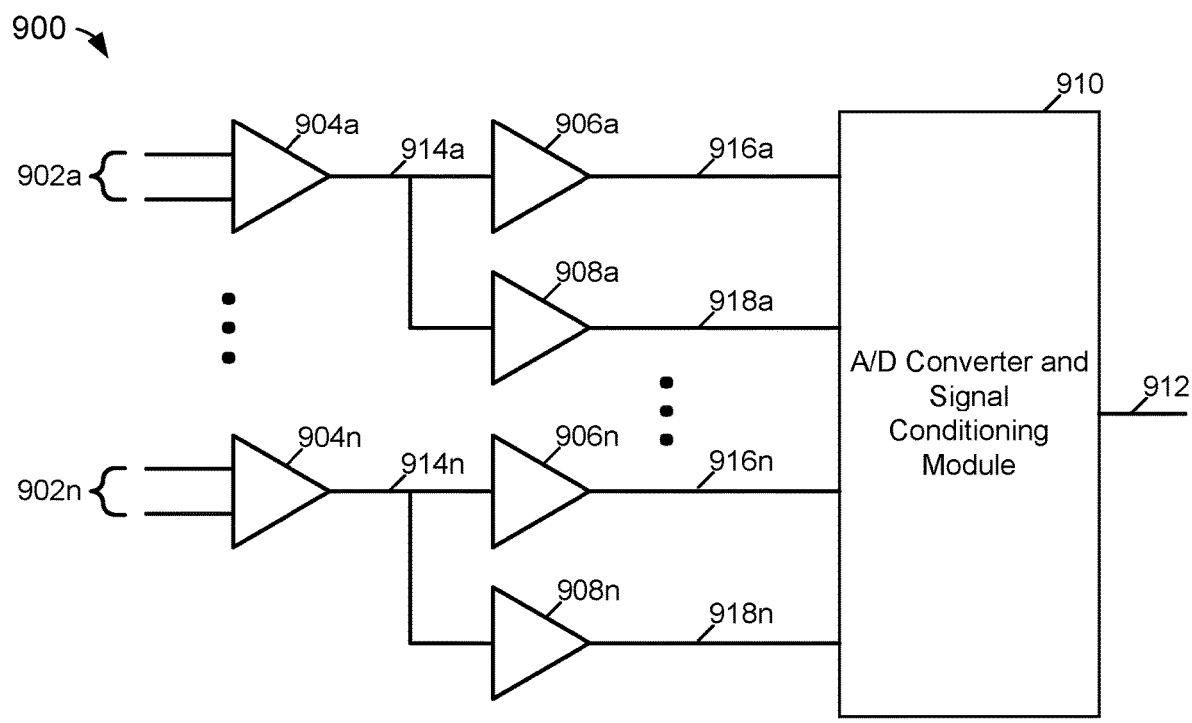
FIG. 9 depicts conditioning circuitry in accordance with at least one example disclosed herein.
Figure 10:
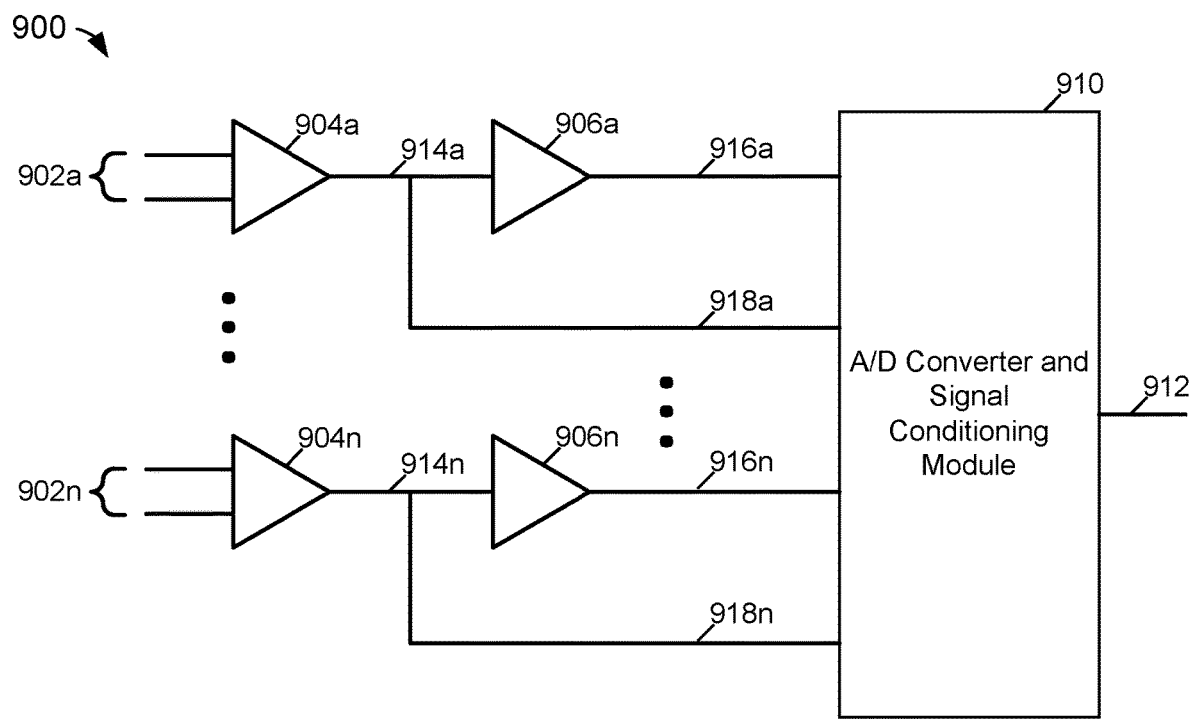
FIG. 10 depicts additional conditioning circuitry in accordance with at least one example disclosed herein.

As explained above, some examples disclosed herein enable rapid recovery of sensory function by leveraging two or more circuit paths of multiple circuit paths, each of which is designed to process signals acquired under different conditions. FIGS. 9 and 10, which are described further below, illustrate examples of these circuit paths. In these examples, the cardiac monitor and the treatment controller described above with reference to FIG. 2 are configured to utilize these different circuit paths within a monitoring and treatment process as illustrated in FIG. 8.

Figure 8:
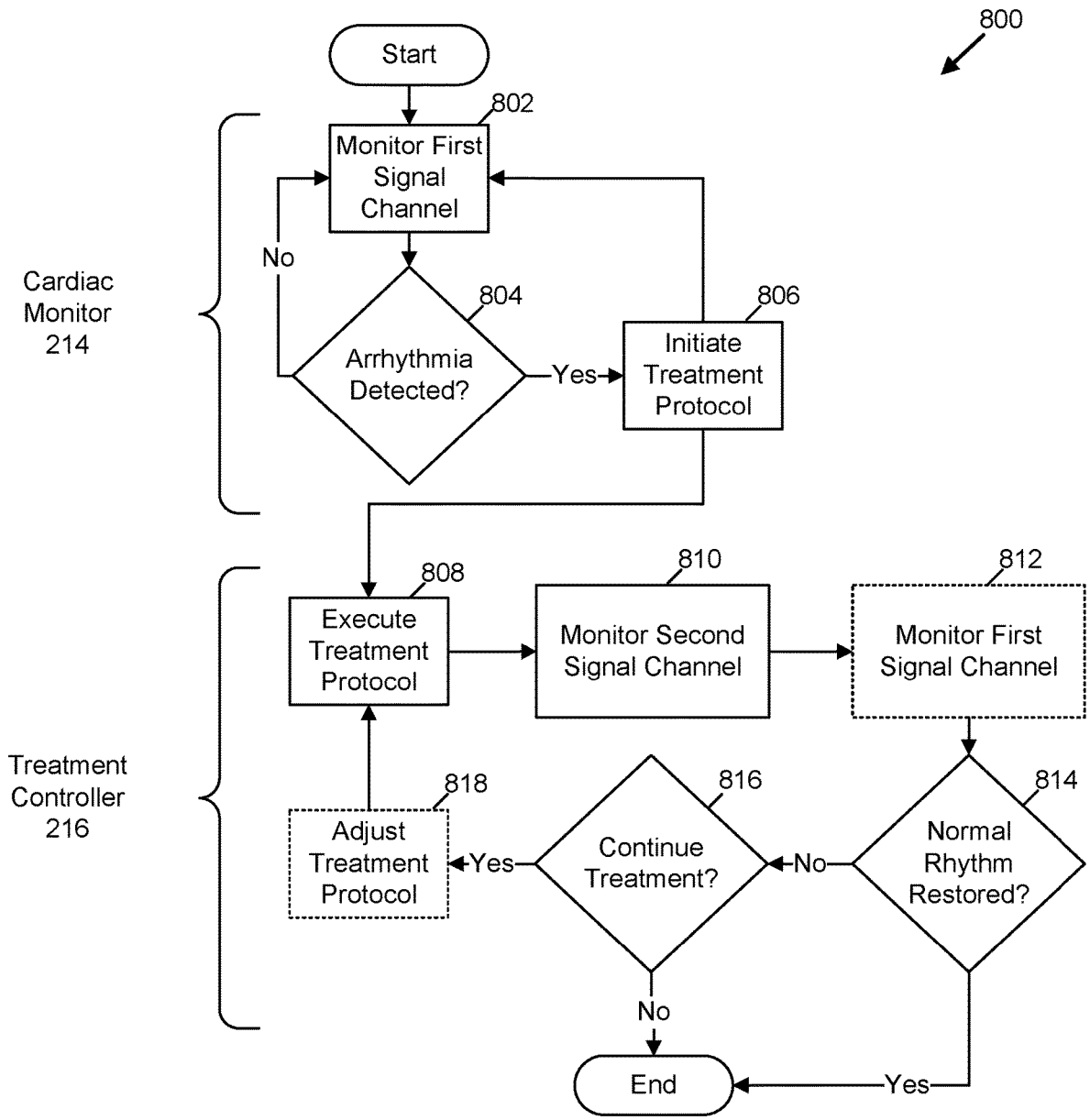
FIG. 8 depicts another monitoring and treatment process in accordance with at least one example disclosed herein.

More specifically, FIG. 8 depicts a monitoring and treatment process 800 executed jointly by the cardiac monitor and the treatment controller. The monitoring and treatment process 800 starts in the act 802 with the cardiac monitor monitoring ECG data received via a first circuit path. In some examples, the circuitry that acts as a conduit of this ECG data includes the sensing electrodes of the first type (e.g., conductive electrodes) and the sensor interface. The sensor interface includes a plurality of circuits that each condition acquired ECG signals in a different manner. For instance, the conditioning circuitry of a second circuit path is configured to process signals acquired near the provision of each therapeutic stimulation pulse, and the conditioning circuitry of the first circuit path is configured to process signals acquired not near the provision of each therapeutic stimulation pulse. FIG. 9 illustrates one example of these circuits and is described further below. Alternatively or in addition, the conditioning circuitry of the first circuit path is configured to process signals acquired during a monitoring period when the device is analyzing ECG signals to detect arrhythmias, the conditioning circuitry of the second circuit path is configured to process ECG signals acquired during a treatment period, e.g., when the device is delivering pacing pulses to the patient, and monitoring for capture.

In act 804, the cardiac monitor determines whether the ECG data indicates that the patient is experiencing an arrhythmia. In some examples, the cardiac monitor uses ECG data generated via the high gain signal path for such monitoring. This ECG data may be representative of ECG signals in a range from approximately 50 µV to approximately 5 mV. As such, the first circuit path may include high gain circuit elements as part of the signal conditioning circuitry. For example, the gain can be between around 100 to around 1000 (assuming a 5V circuit rails). If an arrhythmia is detected, the cardiac monitor initiates a treatment protocol in act 806 by calling the treatment controller. Arrhythmias that can trigger a treatment protocol include bradycardias, tachycardias, and fibrillations. In some examples, the cardiac monitor identifies a bradycardia condition where the patient's heart rate drops to below a predetermined threshold (e.g., 40 beats per minute) for a sustained period of time (e.g., 30 seconds). In some examples, the cardiac monitor identifies a tachycardia condition where the patient's heart rate elevates to beyond a predetermined threshold (e.g., 40 beats per minute) for a sustained period of time (e.g., 30 seconds). Such thresholds and time periods can be configured for each patient depending on the patient history. If the cardiac monitor does not detect an arrhythmia in the act 804, the cardiac monitor returns to the act 802.

In the act 808, the treatment controller executes a treatment protocol. When executing the treatment protocol, the treatment controller may coordinate and control various components of the medical device to provide treatment to the patient. For example, such a treatment protocol can be a pacing protocol where the medical device provides pacing pulses to the patient. In certain examples, the treatment controller executes a pacing protocol in response identifying a bradycardia condition or a tachycardia condition. In some examples, the treatment protocol can be a defibrillation protocol where the medical device provides defibrillation pulses to the patient. For example, arrhythmia conditions that could trigger a defibrillation protocol include ventricular tachycardia or ventricular fibrillation. For example, the treatment controller may provide one or more therapeutic stimulation pulses, such as pacing pulses and/or defibrillating shocks, to the patient's body via the therapy electrodes. Prior to providing the one or more therapeutic stimulation pulses, in some examples, the treatment controller may signal a gel dispenser housed in a therapy pad to dispose electrically conductive gel between the skin of the patient and a therapy electrode.

In act 810, the treatment controller can expect to see pacing spikes across the ECG electrode and as such switches to monitoring the received ECG data over the lower gain, second circuit path. In one example, the lower gain circuit path is configured to monitor ECG signals in a range of from approximately 0.5 mV to approximately 5 mV. The gain can be generally lower than the gain of the first circuit path (e.g., in a range of between around 50 to around 500). Depending on circuit design and circuit element selection, the actual gain values can vary. It is understood, however, that the second circuit path will be configured to have lower gain than the first circuit path, and consequently have faster transient recovery characteristics than the first circuit path. In this regard, such a low gain circuit path can process signals in this range along with quick recovery from high voltage transients caused from pacing spikes that could be up to 700 mV. The pacing transients may have higher amplitudes than 700 mV (e.g., up to a volt or more), but the electrode input circuitry can include clamping diodes that limit the input voltages to around +/−700 mV. Because the conditioning circuitry of the second circuit path is configured to condition data received near the provision of a therapeutic stimulation pulse, the second circuit path is able to provide meaningful ECG data more quickly following the provision of a therapeutic stimulation pulse than the first circuit path.

In some examples, optionally, as shown in act 812, the treatment controller may switch between the first and second circuit paths dynamically during execution of the treatment protocol. For instance, the treatment controller may first monitor ECG data using the second circuit path (low gain) during a period covering the provision of a therapeutic stimulation pulse and soon thereafter (e.g., within about 200 ms or more, depending on circuit design). After this period has passed, in some situations, the treatment controller may switch to monitoring ECG data using the first circuit path (high gain). For example, if the medical device is configured to suspend the provision of the therapeutic stimulation pulses for a period of time, the treatment controller may switch to the first circuit path.

In act 814, the treatment controller determines whether the ECG data indicates that the patient's normal cardiac rhythm has been restored. If so, the treatment controller terminates its portion of the monitoring and treatment process 800. If the treatment controller does not detect restoration of the patient's normal cardiac rhythm in the act 814, the treatment controller proceeds to act 816.

In the act 816, the treatment controller determines whether treatment of the patient should continue. For example, within the act 816, the treatment controller may determine whether execution of the treatment protocol has continued for longer than a threshold duration or for more than a threshold number of cycles. Also, within the act 816, the treatment controller may determine whether the medical device has sufficient resources available to continue execution of the treatment protocol (e.g., whether sufficient battery power remains). If, in the act 816, the treatment controller determines that treatment of the patient should not continue, the treatment controller terminates its portion of the monitoring and treatment process 800. If, in the act 816, the treatment controller determines that treatment of the patient should continue, the treatment controller optionally proceeds to act 818.

In the act 818, the treatment controller determines whether any adjustments to the treatment protocol should be made. For example, within the act 818, the treatment controller may analyze the ECG data received via the second circuit path within the act 810 to determine adjustments to make to the characteristics of therapeutic stimulation pulses provided by the therapy electrode. These characteristics may include level of current, pulse width, pulse rate, and waveform among other characteristics. Adjustments identified with in the act 818 may be based on an inability of the treatment protocol to capture, cardiovert, or defibrillate the patient. In some examples, the treatment controller may be able to make beneficial adjustments to the treatment protocol more quickly than otherwise would be possible due to the early availability of accurate ECG data via the second circuit path. After appropriately adjusting the treatment protocol, the treatment controller returns to the act 808 and continues to treat the patient.

Examples implementing the monitoring and treatment process 800, are able to execute treatment protocols using ECG data that more completely covers the patient's cardiac activity during, and in response to, treatment.

FIG. 9 illustrates an example schematic of a circuit 900 configured to acquire signals from sensing electrodes, in accordance with an example. All or portions of the circuit 900 may be implemented, for example, in the connection pod 130 of FIG. 1, and may further be electrically coupled to one or more of the sensing electrodes 112 of FIG. 1. The circuit 900 includes one or more electrical leads 902a-902n, one or more analog differential amplifiers or circuits 904a-904n, two or more analog signal path amplifiers 906a-906n and 908a-908n, an analog-to-digital (A/D) converter and signal conditioning module 910, and a digital signal output 912. The electrical leads 902a-902n are paired inputs (e.g., a positive line input and a negative line input) electrically coupled to sensing electrodes (e.g. the sensing electrodes 112). In some examples, at least some of the leads 902a-902n can be electrically coupled to single line electrodes (e.g., one input from the electrode and one input from a separate reference signal or ground). Further, in some examples, one or more of the electrical leads 902a-902n can each be coupled to multiple sensing electrodes.

The analog differential amplifiers 904a-904n are configured to receive the analog input signals from each of the respective leads 902a-902n and to generate a differential output signal 914a-914n. Each of the differential output signals 914a-914n is then split into at least two separate signal paths 916a-916n and 918a-918n. Each signal path 916a-916n and 918a-918n includes one of the signal path amplifiers 906a-906n and 908a-908n, respectively. In particular, the signal path amplifiers 906a-906n are configured to provide a different gain to the differential output signal 914a-914n in the first signal path 916a-916n than the signal path amplifiers 908a-908n provide to the differential output signal 914a-914n in the second signal path 918a-918n. For example, the differential output signal 914a in the first signal path 916a may be amplified by the corresponding signal path amplifier 906a by an order of magnitude more than the differential output signal 914a in the second signal path 918a is amplified by the corresponding signal path amplifier 908a. For example, the first signal path may provide gain of about 100 to about 1000, while the second signal path may provide a gain of about 10 to about 500. Depending on circuit design and configuration, other gain values are possible. It is understood, however, that the second circuit for detecting and monitoring pacing capture includes lower gain circuit elements in order to speed up circuit recovery following saturation (e.g., by a pacing transient). Additional circuits with varying gains are possible. In operation, the processor can dynamically switch between the different circuits to determine an appropriate gain setting to determine capture. For example, the processor can have a default gain setting for arrhythmia monitoring, and switch to other gain modes or circuit paths during a treatment period to identify evidence of capture.

In some cases, such as shown in FIG. 10, the differential output signal 914a-914n may have zero (or nearly zero) gain in one of the signal paths 916a-916n or 918a-918n (e.g., the corresponding signal path amplifier 906a-906n or 908a-908n is effectively or actually a short circuit between the corresponding analog differential amplifier 904a-904n and the A/D converter and signal conditioning module 910). In some cases, one or more of the signal path amplifiers 906a-906n and 908a-908n can provide a signal gain that is programmable by a user or programmable by another component of the medical device (such as the medical device controller 120 of FIG. 1). Such a programmable signal path amplifier may include, for example, the MAX9939 general-purpose, differential-input programmable-gain amplifier (PGA) sold by Maxim Integrated Products, Inc., of San Jose, Calif., or another suitable PGA device.

As a result of splitting and, in some cases, amplifying the differential output signal 914a-914n into the two signal paths 916a-916n and 918a-918n, the A/D converter and signal conditioning module 910 receives the differential output signal 914a-914n from the respective lead 902a-902n at two different gain levels. The A/D converter and signal conditioning module 910 processes and digitizes one or more of the differential output signals 914a-914n from the first signal path 916a-916n, the second signal path 918a-918n, or both to generate the digital signal output 912. For example, the digital signal output 912 may include a digitized representation of the voltages of the analog input signals from one or more of the respective leads 902a-902n. The digital signal output 912 can be provided to another portion of the medical device (or another medical device), such as a cardiac monitor or treatment controller, for further processing.

According to an example, the A/D converter and signal conditioning module 910 converts the differential output signal 914a-914n from both the first signal path 916a-916n and the second signal path 918a-918n into the digital signal output 912. According to another example, the A/D converter and signal conditioning module 910 selectively converts the differential output signal 914a-914n from the first signal path 916a-916n, the second signal path 918a-918n, or both into the digital signal output 912. Such selection may be performed by the A/D converter and signal conditioning module 910 via a control input from, for example, the medical device controller 120 of FIG. 1, based on certain conditions present in the medical device. For example, the A/D converter and signal conditioning module 910 may be configured to process the differential output signal 914a-914n from the second signal path 918a-918n near and subsequent to provision of one or more therapeutic stimulation pulses (e.g., within approximately 50-300 ms from the peak of a corresponding pulse), and to process differential output signal 914a-914n from the first signal path 916a-916n during non-pacing events at other points, as determined by the medical device controller 120.

Figure 13:
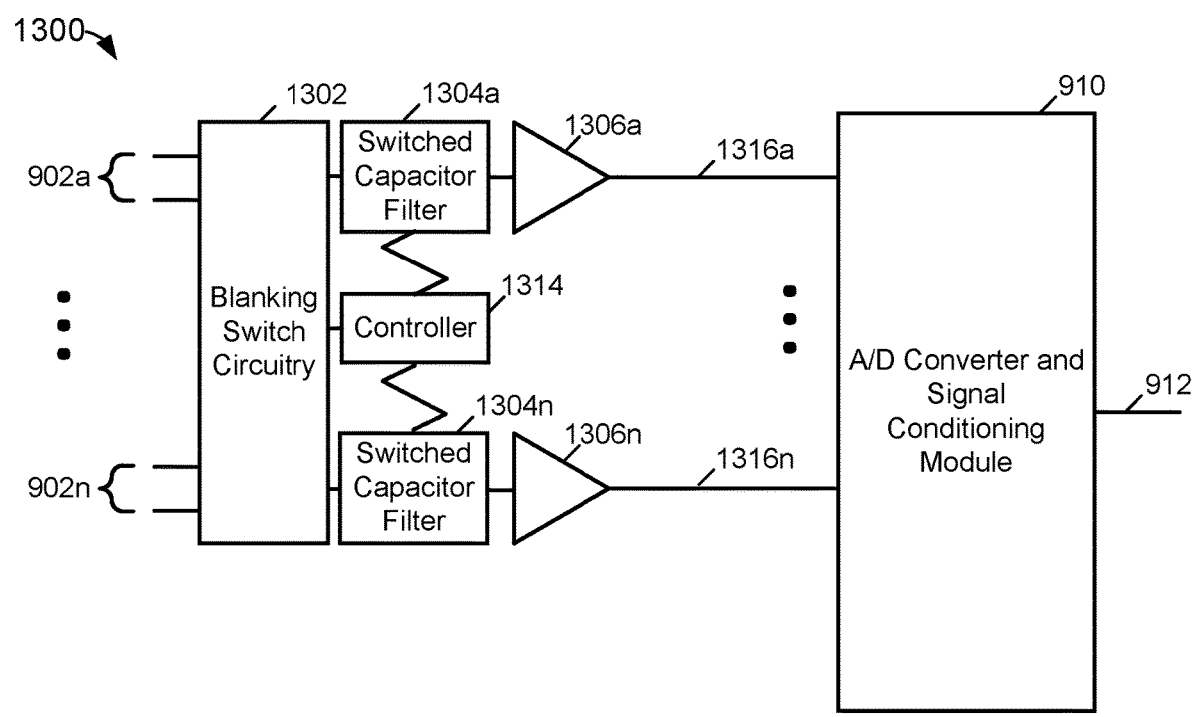
FIG. 13 depicts conditioning circuitry in accordance with at least one example disclosed herein.

FIG. 13 illustrates an example schematic of a circuit 1300 configured to acquire ECG signals from sensing electrodes, in accordance with an example. All or portions of the circuit 1300 may be implemented, for example, in the connection pod 130 of FIG. 1, and may further be electrically coupled to one or more of the sensing electrodes 112 of FIG. 1. The circuit 1300 includes the one or more leads 902a-902n, blanking switch circuitry 1302, one or more switched capacitor filters 1304a-1304n, one or more analog amplifiers or circuits 1306a-1306n, an analog-to-digital (A/D) converter and the signal conditioning module 910, and the digital signal output 912. As shown in FIG. 13, the one or more leads 902a-902n are coupled to the blanking switch circuitry 1302. The blanking switch circuitry 1302 is further coupled to the one or more switched capacitor filters 1304a-1304n. The switched capacitor filters 1304a-1304n are further coupled to the one or more analog amplifiers 1306a-1306n. The one or more analog amplifiers 1306a-1306n are further coupled to the analog-to-digital (A/D) converter and the signal conditioning module 910. The analog-to-digital (A/D) converter and the signal conditioning module 910 is further coupled to the digital signal output 912.

The blanking switch circuitry 1302 is coupled to and controlled by the controller 1314 to selectively couple and decouple the one or more leads 902a-902n to and from the switched capacitor filters 1304a-1304n. For instance, in some examples, the controller 1314 is configured to monitor execution of a treatment protocol and to transmit a first control signal to the blanking switch circuitry 1302 prior to provision of a therapeutic stimulation pulse. The therapeutic stimulation pulse may have a duration of, for example, 40 milliseconds. The blanking switch circuitry 1302 is configured to decouple the one or more leads 902a-902n from the switched capacitor filters 1304a-1304n in response to receiving the first control signal from the controller 1314. In these examples the controller 1314 is also configured to cease transmission of the first control signal and/or to transmit a second control signal to the blanking switch circuitry after provision of the therapeutic stimulation pulse. The blanking switch circuitry 1302 is configured to couple the one or more leads 902a-902n to the switched capacitor filters 1304a-1304n in response to detecting a discontinuance of the first control signal and/or to receiving the second control signal from the controller 1314. In this way, the controller 1314 and the blanking switch circuitry 1302 work in combination to shield the remainder of the components of the circuit 1310 from encountering unwanted effects from the pacing pulses (e.g., amplifier saturation).

The switched capacitor filters 1304a-1304n are coupled to and controlled by the controller 1314 to adjust a passband that attenuates unwanted frequencies within the ECG signals. In some examples, the controller 1314 transmits one or more control signals to the switched capacitor filters 1304a-1304n to indicate a passband to be used by the switched capacitor filters 1304a-1304n. In some examples, this passband includes lower bound and bound upper frequencies within a range of 0.5 hertz to 150 hertz. In some examples, the controller 1314 is configured to shift or otherwise adjust the passband based on the current heart rate of the patient. For instance, in one example, the upper bound may be raised above 150 hertz in according to a function that is directly proportional to the current heart rate of the patient.

The analog signal path amplifiers 1306a-1306n are configured to receive the analog input signals from each of the respective switched capacitor filters 1304a-1304n and to generate an output signal 1316a-1316n. In some examples, one or more of the signal path amplifiers 1316a-1316n can provide a signal gain that is programmable by a user or programmable by another component of the medical device (such as the medical device controller 120 of FIG. 1 or the controller 1314). Such a programmable signal path amplifier may include, for example, the MAX9939 general-purpose, differential-input programmable-gain amplifier (PGA) sold by Maxim Integrated Products, Inc., of San Jose, Calif., or another suitable PGA device.

As explained above, some examples enable rapid recovery of sensory function by disposing electrodes in specific locations. FIG. 12, which is described further below, illustrates one example of these positions. In this example, the cardiac monitor and the treatment controller described above with reference to FIG. 2 are configured to utilize these electrodes within a monitoring and treatment process as illustrated in FIG. 11.

Figure 11:
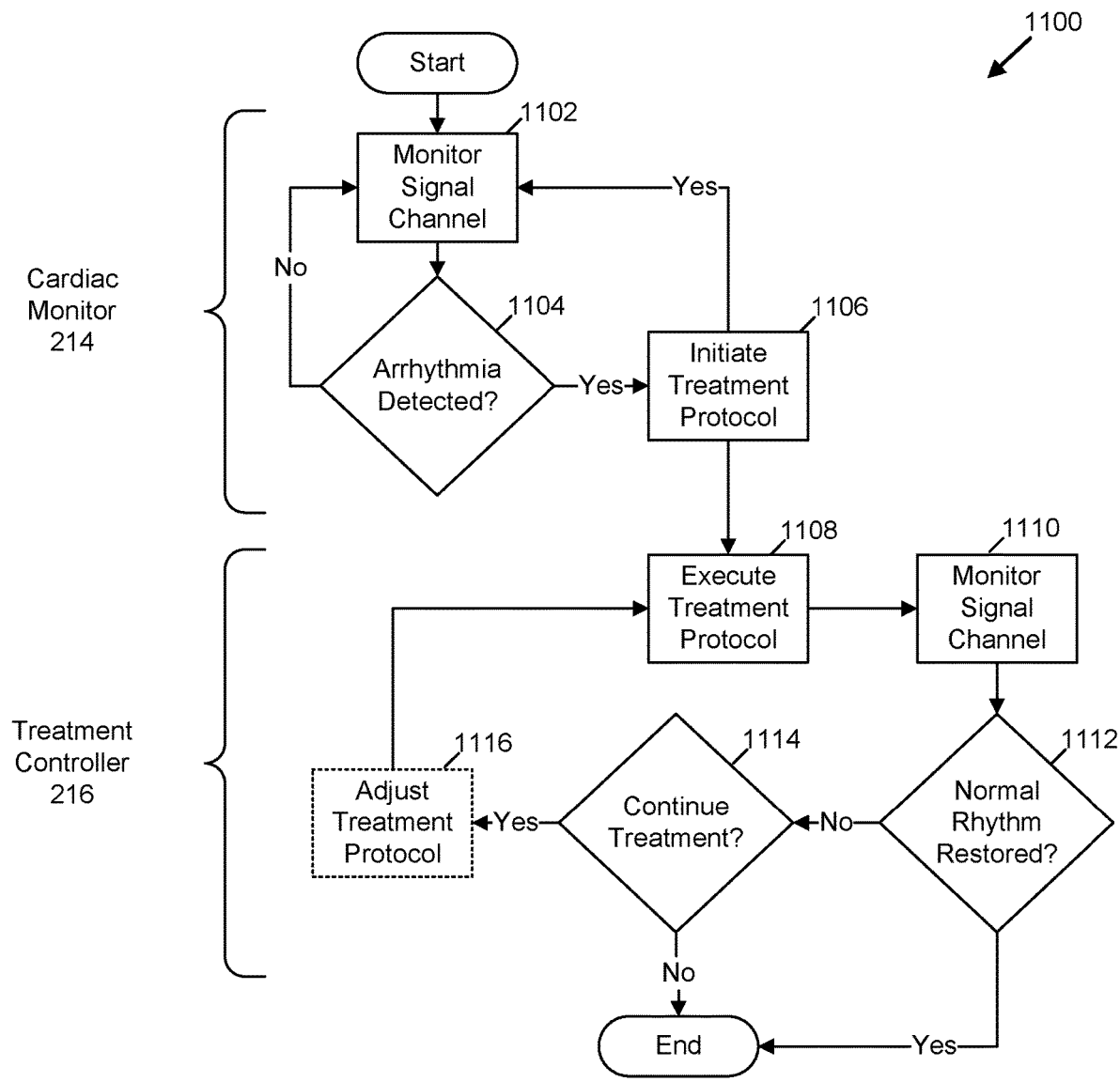
FIG. 11 depicts another monitoring and treatment process in accordance with at least one example disclosed herein.
Figure 12:
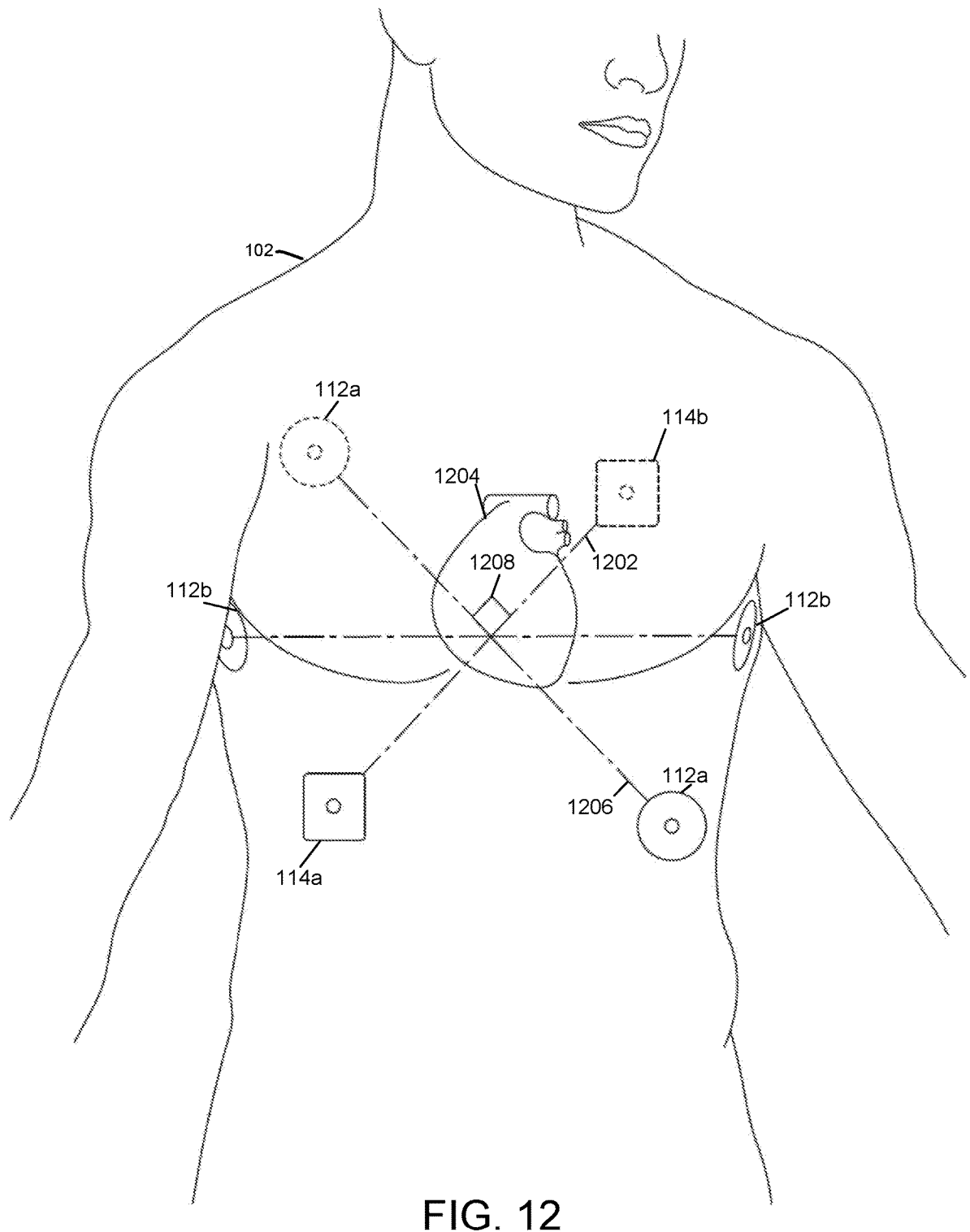
FIG. 12 depicts an arrangement of electrodes in accordance with at least one example disclosed herein.

More specifically, FIG. 11 depicts a monitoring and treatment process 1100 executed jointly by the cardiac monitor and the treatment controller. The monitoring and treatment process 1100 starts in the act 1102 with the cardiac monitor monitoring ECG data received via a signal channel. In some examples, the circuitry that acts as a conduit of this ECG data includes the sensing electrodes and the sensor interface. The sensing electrodes are positioned in specific locations to reduces the amount of energy the sensing electrodes encounter. FIG. 12 illustrates one example of an arrangement of electrodes in these specific locations and is described further below.

In act 1104, the cardiac monitor determines whether the ECG data indicates that the patient is experiencing an arrhythmia. If so, the cardiac monitor initiates a treatment protocol in act 1106. If the cardiac monitor does not detect an arrhythmia in the act 1104, the cardiac monitor returns to the act 1102. In the act 1106, the cardiac monitor calls the treatment controller to initiate its execution of act 1108. In the act 1108, the treatment controller executes a treatment protocol. When executing this treatment protocol, the treatment controller may coordinate and control various components of the medical device to provide treatment to the patient. For example, the treatment controller may provide one or more therapeutic stimulation pulses, such as pacing pulses and/or defibrillating shocks, to the patient's body via the therapy electrodes. Prior to providing the one or more therapeutic stimulation pulses, in some examples, the treatment controller may signal a gel dispenser housed in a therapy pad to dispose electrically conductive gel between the skin of the patient and a therapy electrode.

In act 1110, the treatment controller monitors ECG data received via the signal channel. Because the sensing electrodes of the signal channel are positioned to reduce the amount of energy encountered from one or more therapeutic stimulations pulses, the signal channel is able to provide meaningful ECG data more quickly following the provision of a therapeutic stimulation pulse than the first signal channel. In act 1112, the treatment controller determines whether the ECG data indicates that the patient's normal cardiac rhythm has been restored. If so, the treatment controller terminates its portion of the monitoring and treatment process 1100. If the treatment controller does not detect restoration of the patient's normal cardiac rhythm in the act 1112, the treatment controller proceeds to act 1114.

In the act 1114, the treatment controller determines whether treatment of the patient should continue. For example, within the act 1114, the treatment controller may determine whether execution of the treatment protocol has continued for longer than a threshold duration or for more than a threshold number of cycles. Also, within the act 1114, the treatment controller may determine whether the medical device has sufficient resources available to continue execution of the treatment protocol (e.g., whether sufficient battery power remains). If, in the act 1114, the treatment controller determines that treatment of the patient should not continue, the treatment controller terminates its portion of the monitoring and treatment process 1100. If, in the act 1114, the treatment controller determines that treatment of the patient should continue, the treatment controller optionally proceeds to act 1116.

In the act 1116, the treatment controller determines whether any adjustments to the treatment protocol should be made. For example, within the act 1116, the treatment controller may analyze the ECG data received via the signal channel within the act 1110 to determine adjustments to make to the characteristics of therapeutic stimulation pulses provided by the therapy electrode. These characteristics may include level of current, pulse width, pulse rate, and waveform among other characteristics. Adjustments identified with in the act 1116 may be based on an inability of the treatment protocol to capture, cardiovert, or defibrillate the patient. In some examples, the treatment controller may be able to make beneficial adjustments to the treatment protocol more quickly than otherwise would be possible due to the early availability of accurate ECG data via the second signal channel. After appropriately adjusting the treatment protocol, the treatment controller returns to the act 1108 and continues to treat the patient.

Examples implementing the monitoring and treatment process 1100, are able to execute treatment protocols using ECG data that more completely covers the patient's cardiac activity during, and in response to, treatment.

FIG. 12 illustrates an arrangement of electrodes 1200 configured to reduce the amount of energy encountered by the sensing electrodes 112a when, for example, the therapy electrodes 114a and 114b provide one or more therapeutic pulses to the patient 102. As shown in FIG. 12, the therapy electrodes 114 are arranged to form a current path 1202 that traverses the patient's heart 1204. The sensing electrodes 112a reside along a line 1206 that intersects the current path 1202. The intersection of the current path 1202 and the line 1206 forms angle 1208. In some examples, the angle 1208 is 90 degrees. In some examples, the line 1206 bisects the current path 1202. In some examples one or both of the sensing electrodes 112a are equidistant from one or both of the therapy electrodes 114. In some examples, the electrodes 112a and 114 are embedded within a garment, such as the garment 110, that generally positions the electrodes in the locations illustrated in FIG. 12 vis-à-vis the patient 102.

Additional Examples

Several examples incorporate various combinations of the features described above to advantageous effect. For instance, in some examples, the electrodes of a medical device are both differentiated, as described above with reference to FIGS. 3-7 and specifically located to reduce encountered energy, as described above with reference to FIGS. 11 and 12. In some examples, the medical device incorporates both differentiated electrodes and differentiated signal channels, as described above with reference to FIGS. 8-10. In some examples, the medical device incorporates differentiated signal channels and specifically located electrodes. In some examples, the medical device incorporates differentiated signal channels and differentiated and specifically located electrodes.

Although the subject matter contained herein has been described in detail for the purpose of illustration, it is to be understood that such detail is solely for that purpose and that the present disclosure is not limited to the disclosed examples, but, on the contrary, is intended to cover modifications and equivalent arrangements that are within the scope of the appended claims. For example, it is to be understood that the present disclosure contemplates that, to the extent possible, one or more features of any example can be combined with one or more features of any other example.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An ambulatory medical device for measuring a cardiac reaction to one or more therapeutic stimulation pulses, the ambulatory medical device comprising:

at least two sensing electrodes configured to couple externally to a skin of a patient and to acquire first electrocardiogram (ECG) signals from a heart of the patient, the first ECG signals being indicative of an arrhythmia condition of the patient;

pacing circuitry configured to generate at least one pacing pulse;

at least one combined electrode assembly configured to couple externally to the skin of the patient, the at least one combined electrode assembly comprising
- at least one therapy electrode portion configured to provide the at least one pacing pulse to the heart of the patient during execution of a treatment protocol,
- at least one sensing electrode portion configured to acquire second ECG signals from the heart of the patient, the second ECG signals being indicative of a reaction of the heart to the at least one pacing pulse, and
- at least one gel dispenser configured to apply conductive gel between the skin of the patient and the at least one sensing electrode portion to provide at least one gel interface between the skin of the patient and the at least one sensing electrode portion;

signal processing circuitry operably coupled to the at least two sensing electrodes and the at least one combined electrode assembly, the signal processing circuitry configured to
- provide the first ECG signals on a first ECG channel from the at least two sensing electrodes, and
- provide the second ECG signals on a second ECG channel from the at least one combined electrode assembly; and at least one processor coupled to the at least one combined electrode assembly, the pacing circuitry, and the at least two sensing electrodes, the at least one processor configured to
- receive the first ECG signals on the first ECG channel from the signal processing circuitry,
- detect the arrhythmia condition based upon the first ECG signals,
- execute the treatment protocol in response to detection of the arrhythmia condition,
- receive the second ECG signals on the second ECG channel from the signal processing circuitry,
- detect the reaction of the heart to the at least one pacing pulse based upon the second ECG signals acquired from the at least one sensing electrode portion, and
- determine capture of the heart by the at least one pacing pulse based on the reaction.

2. The ambulatory medical device of claim 1, wherein each of the at least two sensing electrodes has a first recovery time and the at least one sensing electrode portion of the at least one combined electrode assembly has a second recovery time that is less than the first recovery time.

3. The ambulatory medical device of claim 2, wherein the first recovery time is between approximately 200 milliseconds and 400 milliseconds and the second recovery time is between approximately 80 milliseconds and 200 milliseconds.

4. The ambulatory medical device of claim 1, wherein the at least one gel dispenser is configured to apply the conductive gel between the skin of the patient and the at least one combined electrode assembly during execution of the treatment protocol to provide a gel interface between the skin of the patient and the therapy electrode portion.

5. The ambulatory medical device of claim 4, wherein the at least one gel interface comprises a first gel interface and a second gel interface electrically isolated from the first gel interface.

6. The ambulatory medical device of claim 1, wherein each of the at least two sensing electrodes comprises a dry sensing electrode portion and the at least one sensing electrode portion of the at least one combined electrode assembly comprises a conductive sensing electrode portion.

7. The ambulatory medical device of claim 1, wherein the at least one processor is further configured to:
- detect if the heart of the patient has returned to a normal cardiac rhythm based upon monitoring the second ECG signals; and
- upon detecting that the heart of the patient has returned to the normal cardiac rhythm, monitor for an additional arrhythmia condition based upon the first ECG signals.

8. The ambulatory medical device of claim 1, wherein detecting the reaction of the heart comprises detecting one or more contractions induced by the at least one pacing pulse.

9. The ambulatory medical device of claim 1, wherein each of the at least two sensing electrodes comprises:
- a first sensing portion configured to acquire the first ECG signals from the heart of the patient; and
- a second sensing portion configured to acquire third ECG signals from the heart of the patient.

10. The ambulatory medical device of claim 9, wherein the first sensing portion and the second sensing portion are electrically isolated.

11. The ambulatory medical device of claim 9, wherein the first sensing portion has a first recovery time and the second sensing portion has a second recovery time that is less than the first recovery time.

12. The ambulatory medical device of claim 11, wherein the first recovery time is between approximately 200 milliseconds and 400 milliseconds and the second recovery time is between approximately 80 milliseconds and 200 milliseconds.

13. The ambulatory medical device of claim 9, wherein each of the at least two sensing electrodes further comprises a gel dispenser configured to apply conductive gel between the skin of the patient and the second sensing portion during execution of the treatment protocol to provide a gel interface between the skin of the patient and the additional second sensing portion.

14. The ambulatory medical device of claim 9, wherein the first sensing portion comprises a dry sensing electrode portion and the second sensing portion comprises a conductive sensing electrode portion.

15. An ambulatory medical device for measuring a cardiac reaction to one or more therapeutic stimulation pulses, the ambulatory medical device comprising:
- at least two sensing electrodes configured to couple externally to a skin of a patient and to acquire first electrocardiogram (ECG) signals from a heart of the patient, the first ECG signals being indicative of an arrhythmia condition of the patient;
- pacing circuitry configured to generate at least one pacing pulse;
- at least one combined electrode assembly configured to couple externally to the skin of the patient, the at least one combined electrode assembly comprising
  - at least one therapy electrode portion configured to provide the at least one pacing pulse to the heart of the patient during execution of a pacing protocol, and
  - at least one sensing electrode portion configured to acquire second ECG signals from the heart of the patient, the second ECG signals being indicative of whether the heart was captured by the at least one pacing pulse;

signal processing circuitry operably coupled to the at least two sensing electrodes and the at least one combined electrode assembly, the signal processing circuitry configured to
- provide the first ECG signals on a first ECG channel from the at least two sensing electrodes, and
- provide the second ECG signals on a second ECG channel from the at least one combined electrode assembly; and at least one processor coupled to the at least one combined electrode assembly, the pacing circuitry, and the at least two sensing electrodes, the at least one processor configured to
- receive the first ECG signals on the first ECG channel from the signal processing circuitry,
- detect the arrhythmia condition based upon the first ECG signals,
- execute the pacing protocol in response to detection of the arrhythmia condition,
- receive the second ECG signals on the second ECG channel from the signal processing circuitry, and
- determine capture of the heart by the at least one pacing pulse based upon the second ECG signals.

16. The ambulatory medical device of claim 15, further comprising:
- at least one gel dispenser configured to apply conductive gel between the skin of the patient and the at least one sensing electrode portion of the at least one combined electrode assembly to provide at least one gel interface between the skin of the patient and the at least one sensing electrode portion.

17. The ambulatory medical device of claim 16, wherein each of the at least two sensing electrodes has a first recovery time and the at least one sensing electrode portion of the at least one combined electrode assembly has a second recovery time that is less than the first recovery time.

18. The ambulatory medical device of claim 17, wherein the first recovery time is between approximately 200 milliseconds and 400 milliseconds and the second recovery time is between approximately 80 milliseconds and 200 milliseconds.

19. The ambulatory medical device of claim 15, wherein the second ECG signals comprise one or more of a widened QRS complex or a changed T wave morphology and thereby indicate the heart was captured by the at least one pacing pulse.

* * * * *